US012788241B2

(12) United States Patent
Yano

(10) Patent No.: US 12,788,241 B2
(45) Date of Patent: Nov. 10, 2026

(54) TEST IMAGE SET FOR TESTING VISUAL CHARACTERISTICS, TEST METHOD FOR VISUAL CHARACTERISTICS, DETERMINING METHOD FOR DETERMINING CHARACTERISTICS OF CORRECTION FILTER, AND CORRECTION FILTER

(71) Applicants: IRIS COMMUNICATION KABUSHIKI KAISHA, Tokyo (JP); NICO CORPORATION, Tokyo (JP)

(72) Inventor: Masafumi Yano, Miyagi (JP)

(73) Assignees: IRIS COMMUNICATION KABUSHIKI KAISHA, Tokyo (JP); NICO CORPORATION, Tokyo (JP)

( * ) Notice: Subject to any disclaimer, the term of this patent is extended or adjusted under 35 U.S.C. 154(b) by 292 days.

(21) Appl. No.: 18/621,609

(22) Filed: Mar. 29, 2024

(65) Prior Publication Data

US 2024/0237892 A1 Jul. 18, 2024

Related U.S. Application Data

(63) Continuation-in-part of application No. PCT/JP2022/036133, filed on Sep. 28, 2022.

(30) Foreign Application Priority Data

Sep. 30, 2021 (JP) ................................ 2021-160960

(51) Int. Cl.
*A61B 3/00* (2006.01)
*A61B 3/032* (2006.01)
*A61B 3/06* (2006.01)

(52) U.S. Cl.
CPC .......... *A61B 3/0325* (2013.01); *A61B 3/0008* (2013.01); *A61B 3/0041* (2013.01); *A61B 3/063* (2013.01); *A61B 3/066* (2013.01)

(58) Field of Classification Search
CPC ... A61B 3/0325; A61B 3/0008; A61B 3/0041; A61B 3/063; A61B 3/066; A61B 3/032
See application file for complete search history.

(56) References Cited

U.S. PATENT DOCUMENTS 6,260,970 B1 * 7/2001 Horn .................... A61B 3/022 351/246
6,536,905 B2 3/2003 Gibb et al.
(Continued)

FOREIGN PATENT DOCUMENTS

EP 3 412 198 A1 12/2018
EP 3 494 867 A1 6/2019
(Continued)

OTHER PUBLICATIONS

Nov. 22, 2022 International Search Report issued in International Patent Application No. PCT/JP2022/036133.
(Continued)

*Primary Examiner* — Mustak Choudhury
(74) *Attorney, Agent, or Firm* — Oliff PLC

(57) ABSTRACT

There is provided a test method for visual characteristics which is less load to a subject and enables testing of visual characteristics of the subject, a test image set for testing visual characteristics, a determining method for determining characteristics of correction filter based on a test result of visual characteristics, and a correction filter made based on it. The test image set includes multiple test images. Each of the multiple test images has a background area and a test area located in the background area. The multiple test images are provided with figures having colors different from a color of the background area in at least one of R, G, or B components in a RGB color space, and the multiple test images are different from each other in colors of at least one of the background area or the test area.

27 Claims, 8 Drawing Sheets

(56) References Cited

U.S. PATENT DOCUMENTS

| | | | | |
|---|---|---|---|---|
| 6,851,809 | B1 * | 2/2005 | Sachtler | A61B 3/066 351/242 |
| 7,106,509 | B2 | 9/2006 | Sharp | |
| 7,193,780 | B2 | 3/2007 | Wada et al. | |
| 10,054,803 | B2 | 8/2018 | Wold et al. | |
| 10,331,207 | B1 | 6/2019 | Simmons | |
| 2002/0005936 | A1 * | 1/2002 | Gibb | G02B 7/002 353/84 |
| 2005/0041293 | A1 | 2/2005 | Wada et al. | |
| 2010/0149483 | A1 | 6/2010 | Chiavetta, III | |
| 2010/0165294 | A1 * | 7/2010 | Barbur | A61B 3/0041 351/223 |
| 2010/0179790 | A1 | 7/2010 | Nakauchi et al. | |
| 2012/0162606 | A1 | 6/2012 | Nakamura et al. | |
| 2014/0027653 | A1 | 1/2014 | Mori et al. | |
| 2014/0233070 | A1 | 8/2014 | Kishimoto | |
| 2014/0340641 | A1 | 11/2014 | Edwards et al. | |
| 2015/0199006 | A1 * | 7/2015 | He | A61B 3/113 345/158 |
| 2016/0026005 | A1 | 1/2016 | Flinders | |
| 2019/0167092 | A1 * | 6/2019 | Yano | A61B 3/066 |
| 2020/0310537 | A1 * | 10/2020 | Simmons | G02B 27/0172 |
| 2021/0084731 | A1 | 3/2021 | Yano | |
| 2022/0337319 | A1 * | 10/2022 | Owaki | G02B 5/28 |
| 2022/0400944 | A1 | 12/2022 | Yano | |

FOREIGN PATENT DOCUMENTS

| | | | |
|---|---|---|---|
| JP | H06-018819 | A | 1/1994 |
| JP | 2010-518903 | A | 6/2010 |
| JP | 2012-135528 | A | 7/2012 |
| JP | 2014-160391 | A | 9/2014 |
| JP | 2017-080135 | A | 5/2017 |
| JP | 2019-101345 | A | 6/2019 |
| JP | 2019-209047 | A | 12/2019 |
| WO | 2008/100613 | A2 | 8/2008 |
| WO | 2016/163338 | A1 | 10/2016 |
| WO | 2019/244431 | A1 | 12/2019 |
| WO | 2021/002093 | A1 | 1/2021 |
| WO | 2021/166996 | A1 | 8/2021 |

OTHER PUBLICATIONS

Oct. 3, 2023 International Preliminary Report on Patentability issued in International Patent Application No. PCT/JP2022/036133.

Apr. 27, 2021 International Search Report issued in International Patent Application No. PCT/JP2021/006094.

Jun. 1, 2022 International Preliminary Report on Patentability issued in International Patent Application No. PCT/JP2021/006094.

Feb. 6, 2024 Extended Search Report isued in European Patent Application No. 21756551.4.

U.S. Appl. No. 17/892,988, filed Aug. 22, 2022 in the name of Masafumi Yano.

Ishihara, Shinobu; "The Series of Plates Designed as a Test for Colour-Blindness"; 1972; pp. 1-24; Kanehara Shuppan Co., Ltd.; Tokyo, Japan.

Ishihara, Shinobu; "The Series of Plates Designed as a Test for Colour-Blindness"; Dec. 8, 2020; pp. 1-24; Kanehara Shuppan Co., Ltd.; Tokyo, Japan.

Jun. 23, 2025 Office Action issued in U.S. Appl. No. 17/892,988.

Semrock2018 Master Catalog, Semrock Inc, Rochester, NY, 2018; https://www.yumpu.com/en/document/view/60794266/ semrock-master-catalog-2018 (Year: 2018).

IDEX H&S Store—Product Detail. IDEX Health & Science, www.idex-hs.com/store/product-detail/ff02_460_80_25/fl-004404. Accessed Jun. 17, 2025 (Year: 2025).

Jan. 16, 2026 Office Action issued in U.S. Appl. No. 17/892,988.

Apr. 21, 2026 Office Action issued in U.S. Appl. No. 17/892,988.

* cited by examiner

TEST IMAGE SET FOR TESTING VISUAL CHARACTERISTICS, TEST METHOD FOR VISUAL CHARACTERISTICS, DETERMINING METHOD FOR DETERMINING CHARACTERISTICS OF CORRECTION FILTER, AND CORRECTION FILTER

CROSS-REFERENCE TO RELATED APPLICATION

This is a Continuation-in-Part of International Application No. PCT/JP2022/036133 filed on Sep. 28, 2022, which claims priority from Japanese Patent Application No. 2021-160960 filed on Sep. 30, 2021. The entire disclosures of the prior applications are incorporated herein by reference.

TECHNICAL FIELD

The present disclosure relates to a test image set for testing visual characteristics, a test method for visual characteristics, a determining method for characteristics of correction filter, and a correction filter.

BACKGROUND

As impairments of a human visual sense, there has been known color blindness or color weakness, in which sensitivity to light in a specific wavelength band is low, and photosensitivity, in which people feel dazzled by light in a specific wavelength band. The photosensitivity is, for example, Irlen syndrome. These visual impairments are caused by higher or lower sensitivities of three cone cells (S, M, and L cone cells) or rod cells on a patient's retina compared to normal subjects. These S, M, and L cone cells are cells that respond to blue light, green light, and red light, respectively. The rod cells are cells that respond to the light intensity. The light sensitivity of a human depends on brightness of the environment, and the sensitivity in a bright environment is called photopic vision and the sensitivity in a dark environment is called scotopic vision. The photopic vision is mainly achieved by the cone cells, while the scotopic vision is mainly achieved by the rod cells (see FIGS. 7A-7C). The light sensitivity in an intermediate environment between the two environments is called mesopic vision. Both the cone cells and the rod cells are responsible for the mesopic vision. As a method of correcting the human visual sense of visually impaired patients, there has been known a method using optical filters that light transmission characteristics are adjusted to the patients. The visual abnormality of the patient is suppressed when the patient wears glasses with optical filters of which the characteristics have been adjusted.

In order to make an optical filter adjusted to the patient, it is necessary to test the patient's visual characteristics (sensitivities) to various colors of light. However, since there are countless combinations of sensitivities to various lights, the test of visual characteristics is burdensome for both a testing person and the patient.

There has heretofore been known a method for making optical filters adjusted to the patient. In the method, color vision characteristics are classified into 32 types based on test results of multiple patients' color vision characteristics. Then, it is tested which of the 32 types of color vision characteristics the patient's color vision characteristics correspond to. By determining the characteristics of the optical filter based on the test results, the patient's color vision abnormality is suppressed.

SUMMARY

In the color vision test method described in Patent Document 1, it is determined which of the predefined classifications a patient's color vision characteristic corresponds to. Therefore, there is a problem that accurate test results cannot be obtained for patients with color vision characteristics that do not correspond to any of the predefined classifications, or for patients with intermediate color vision characteristics between the multiple classifications. In the color vision test method described in Patent Document 1, color vision characteristics are classified according to the wavelength range to which cone cells are sensitive, and the sensitivity of rod cells is not taken into consideration. Therefore, the color vision testing method described in Patent Document 1 cannot test for abnormalities in visual characteristics caused by rod cells. In addition, Patent Document 1 does not take into account photopic, scotopic, and mesopic vision, which are affected by the combined sensitivity of cone cells and rod cells.

A test image set according to one embodiment of the present disclosure is a test image set for testing visual characteristics of a subject, the test image set including a plurality of test images, each of the plurality of test images including a background area, and a test area located in the background area, the test area including a figure having a color different from a color of the background area in at least one of R, G or B components in a RGB color space, and the plurality of test images are different from each other in the color of at least one of the background area or the test area.

A test method for visual characteristics according to one embodiment of the present disclosure is a test method for visual characteristics of a subject using test images included in a test image set described above. The test method for visual characteristics comprising a showing step of sequentially showing the test images included in the test image set to the subject, and a determining step of determining whether a particular test condition is specified when the subject looks at each of the test images sequentially shown in the showing step.

A determining method according to one embodiment of the present disclosure is a determining method for determining characteristics of a correction filter using the test image set described above. The determining method comprises sequentially showing the test images included in the test image set to the subject, determining whether a particular test condition is satisfied when the subject looks at each of the test images sequentially shown, specifying, among the test images, at least one test image that satisfies the particular test condition, and determining transmittance of a correction filter configured to adjust an intensity of transmitted light based on a color of the specified at least one test image.

A correction filter according to one embodiment of the present disclosure has the transmittance determined by the determining method described above.

DETAILED DESCRIPTION OF THE EMBODIMENT

Hereinafter, an illustrative embodiment according to aspects of the present disclosure will be described referring to the accompanying drawings.

[Test System of Visual Characteristics]

Figure 1:
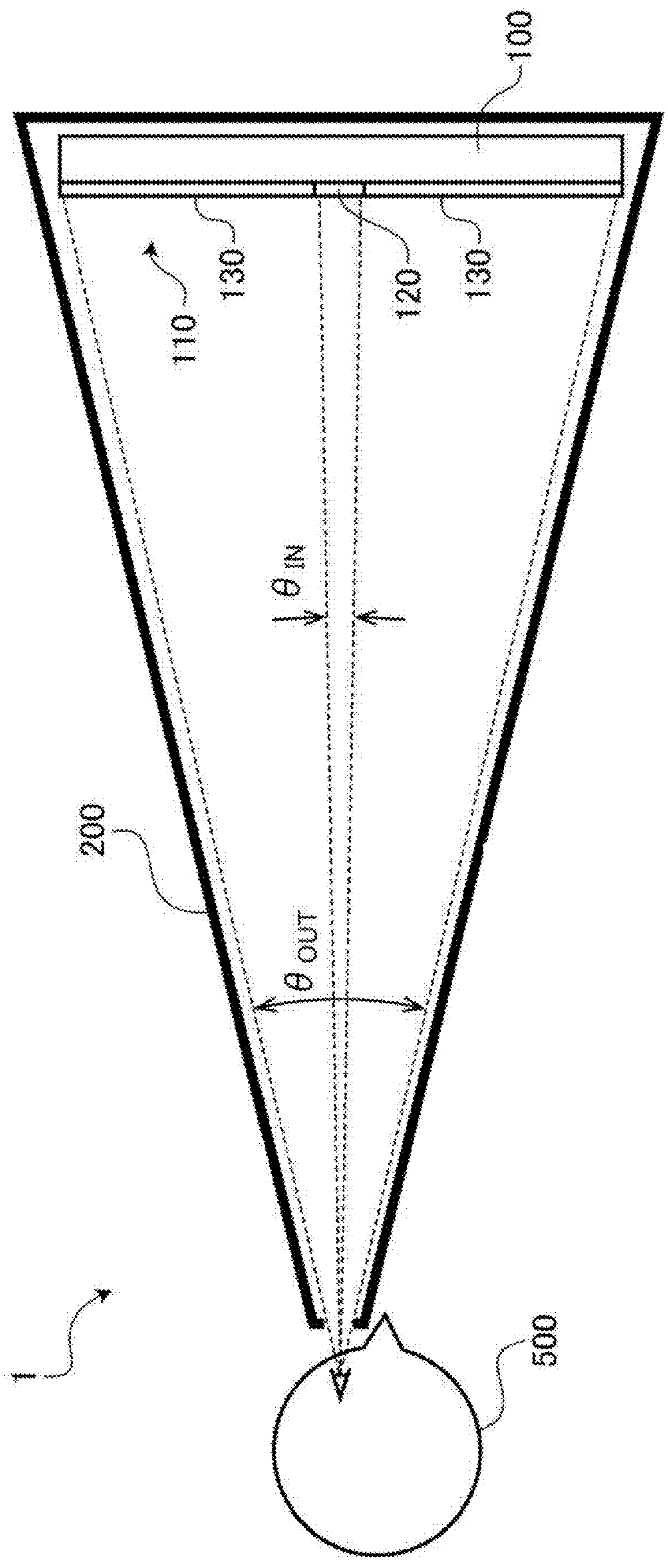
FIG. 1 is a schematic diagram of a test system of visual characteristics according to aspects of the present disclosure.

FIG. 1 is a schematic diagram of a test system of visual characteristics 1 for performing a test of visual characteristics according to one embodiment of the present disclosure. The test system of visual characteristics 1 is equipped with a display 100, a light shielding hood 200, and is used to test the visual characteristics of a subject 500.

The display 100 is, for example, a liquid crystal display or a CRT (Cathode Ray Tube) display. The display 100 displays a test image 110. The display 100 is used to show the test image 110 to the subject 500. The display 100 is not limited to the liquid crystal display that displays an image based on image signals. For example, the display 100 is equipped with a film on which the test image 110 is printed and a backlight that illuminates the film. The test image 110 may be presented to the subject 500 by illuminating the film with illumination light.

The display 100 is covered with the light shielding hood 200. The light shielding hood 200 is configured to prevent the test image 110 from being illuminated by external light and changing the luminance and color of the test image 110 as seen by the subject 500. The inside of the light shielding hood 200 should be black, which absorbs light, in order to prevent light from reflecting and affecting the test of visual characteristics.

In the test of visual characteristics, the subject 500 looks at the test image 110 with one or both eyes. The degree to which the subject 500 perceives glare in the test image 110 (i.e., the degree of photosensitivity that the subject 500 has) and the color of the test image 110 (i.e., the color vision characteristics of the subject 500) are tested.

Once the visual characteristics of the subject 500 are tested by the test of visual characteristics, a correction filter can be made to correct the visual characteristics of the subject based on the test results. The test results may be used not only to made the correction filter, but also to adjust the luminance and color of a lighting system or a monitor, such as a television or a mobile terminal used by the subject 500, to match the visual characteristics of the subject 500.

Figure 2:
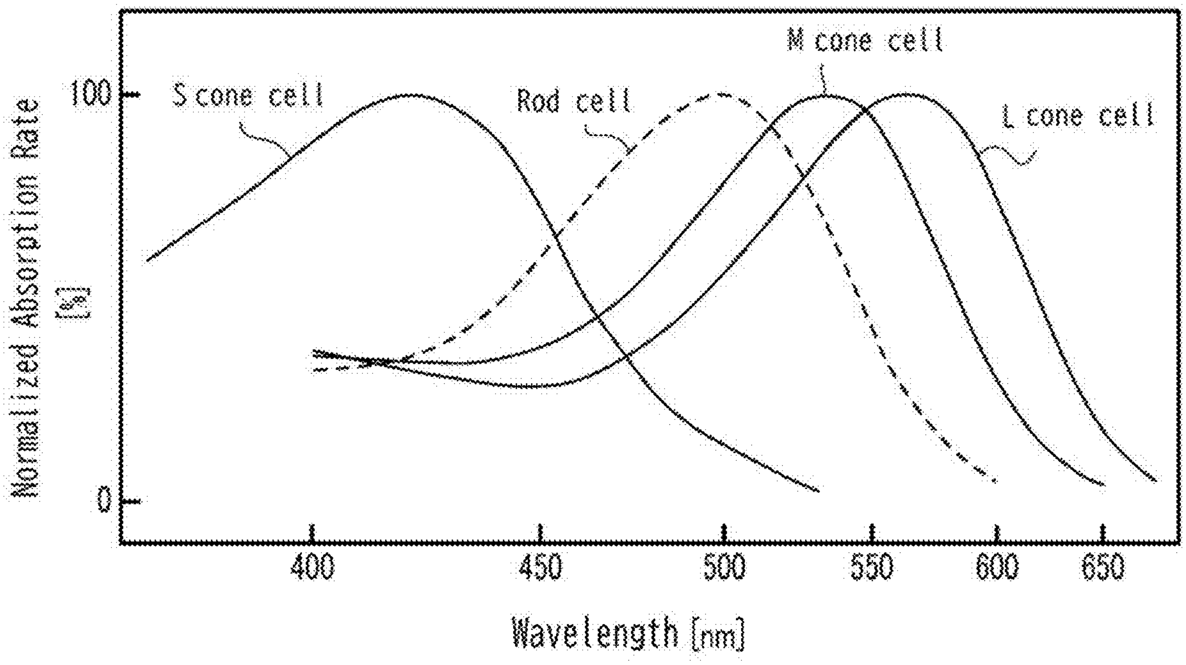
FIG. 2 shows an example of absorption spectra of human cone cells (S cone cells, M cone cells, and L cone cells) and rod cells.

FIG. 2 shows an example of absorption spectra of human cone cells (S cone cells, M cone cells, and L cone cells) and rod cells. The horizontal axis in FIG. 2 indicates the wavelength of light, and the vertical axis indicates absorption rates of the cone cells and rod cells. In FIG. 2, "S," "M," "L," and "Rod" indicates the S cone cells, the M cone cells, the L cone cells, and the rod cells, respectively. Each absorption spectrum shown in FIG. 2 is normalized by the maximum value of absorptivity. The higher the absorptivity of each of the cone cells and the rod cells, the more sensitive it is to light. The S cone cells have a maximum sensitivity at a wavelength of about 420 nm. The M cone cells have maximum sensitivity at a wavelength of about 534 nm. The L cone cells have a maximum sensitivity at a wavelength of about 564 nm. The rod cells have a maximum sensitivity at a wavelength of about 498 nm. The wavelength at which each of cone and rod cells has the maximum sensitivity varies depend on individuals.

Figure 3:
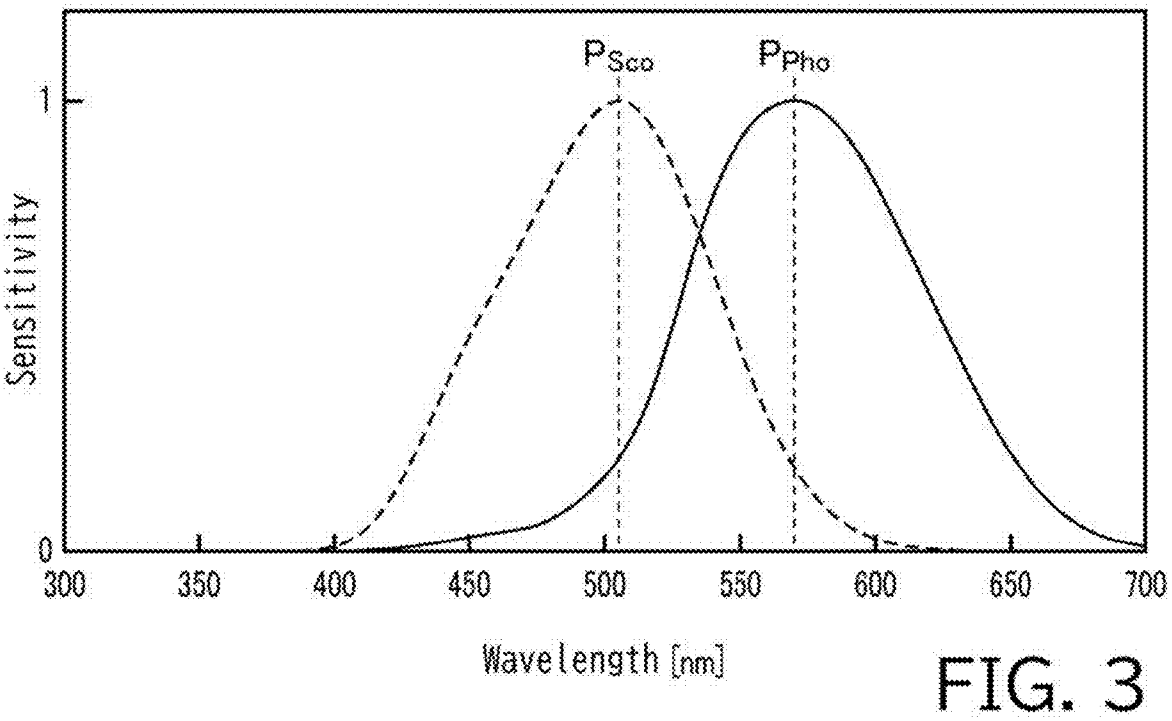
FIG. 3 shows the photopic and scotopic visions of a human.

FIG. 3 shows the photopic and scotopic visions of a human. The horizontal axis of FIG. 3 shows the wavelength of light, and the vertical axis shows sensitivities of a human at each wavelength. The photopic vision is indicated by a solid line and the scotopic vision is indicated by a dashed line. The human's sensitivity to light differs between light and dark areas. Since the cone cells are mainly responsible for the photopic vision, it is thought that in the light area, the human recognize colors with M and L cone cells, and recognize light luminance with the remaining S cone cells. On the other hand, since the rod cells are mainly responsible for the scotopic vision, it is thought that in the dark area, the human recognize the luminance of light by the rod cells. Therefore, the human, whose the S cone cells and the rod cells have high sensitivity, which are used to recognize the luminance of light, have a symptom of photosensitivity, in which they feel dazzled by light. In addition, a human with differences in the sensitivity of M and L cone cells used for color perception (i.e., sensitivity to green light and sensitivity to red light) have a symptom of color weakness or color blindness. The color weakness includes, for example, a first type of color weakness with low sensitivity to red light and a second type of color weakness with low sensitivity to green light.

[Test Image Set]

Figure 4:
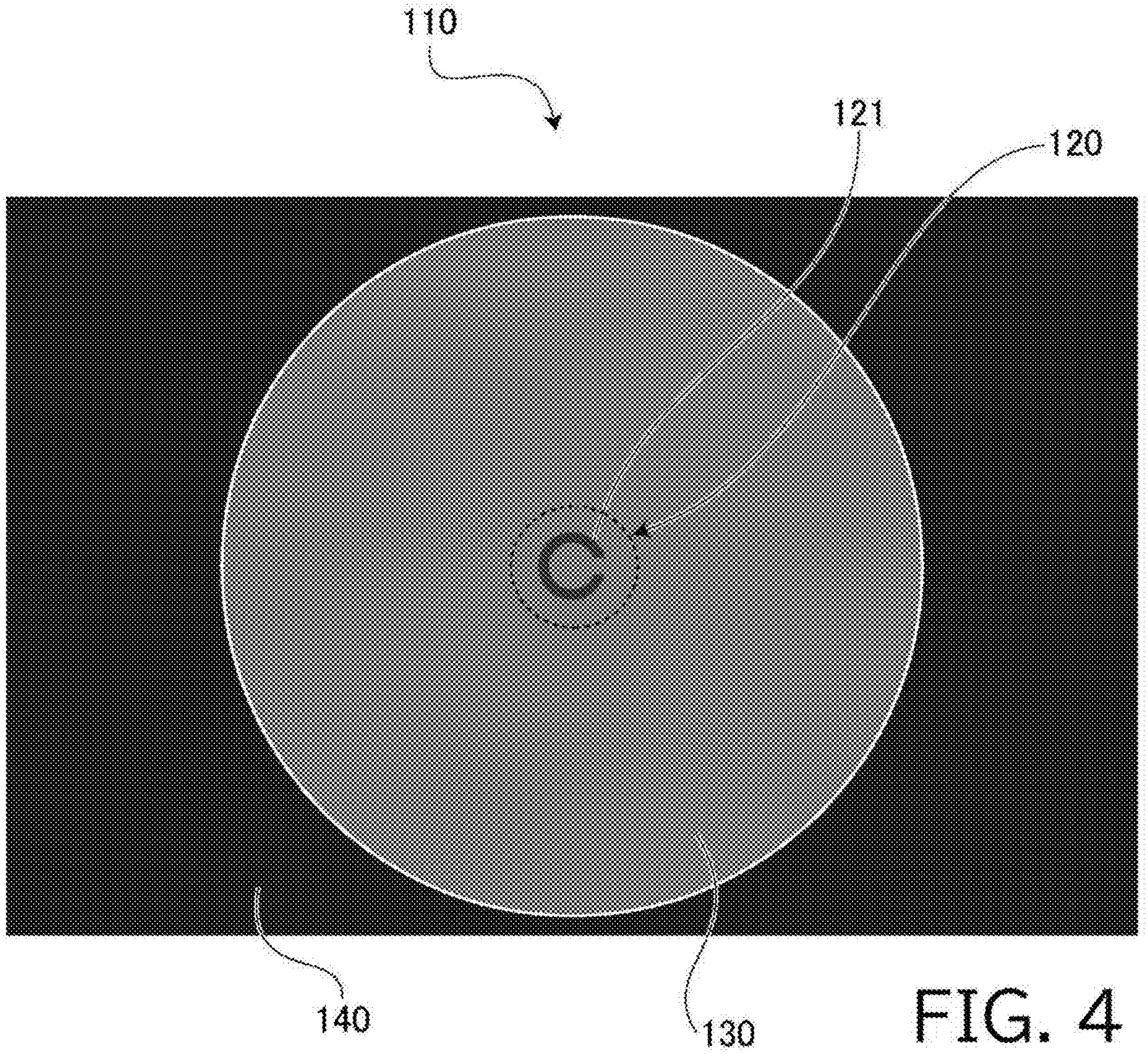
FIG. 4 shows an example of a test image according to aspects of the present disclosure.

Next, test image sets will be explained. The test image set is a set of multiple test images. The test images are displayed on the display 100. FIG. 4 shows an example of a test image 110.

The test image 110 has a test area 120 located around a center of the test image 110 and a background area 130 surrounding the test area 120. In FIG. 4, the test area 120 is surrounded by a dashed line. This dashed line is drawn to explain the test area 120 and is not included in the test image 110. A figure 121 is arranged in the test area 120. The figure 121 and the background area 130 have different colors. An area is the test area 120 other than the FIG. 121 (i.e., an area, in the test area, where the figure is not located) has the same color as the background area 130. In the example shown in FIG. 4, the background area 130 has a circular figure. A peripheral area 140 further outside of the background area 130 is black.

In the example in FIG. 4, the figure 121 is a Landolt ring, which is normally used in an eyesight test, but the embodiment of the present application is not limited to this. The FIG. 121 may be any figure that a person can recognize, such as characters, numbers, circles, squares, or other figures. The figure 121 may be a combination of multiple letters or figures.

The test area 120 is an area corresponding to a fovea centralis on a human retina. The size of the test area 120 is set in such a manner that light emitted from the test area 120 forms an image within the fovea centralis. For example, the size of the test area 120 is set so that the apex angle $\theta_{IN}$ (see FIG. 1) of the cone with the test area 120 as the base and the eyes of the subject 500 as the vertices is about 2 degrees. This apex angle $\theta_{In}$ of about 2 degrees corresponds to width of the field of view by the fovea centralis (i.e., the viewing angle). The diameter of the test area 120 depends on the distance between the subject 500 and the display 100 of the test system of visual characteristics 1. The size of the test area 120 should be set so that light emitted from the test area 120 forms an image within the fovea centralis, and the apex angle $\theta_{In}$ need not be exactly 2 degrees. Therefore, light emitted from the figure 121 located in the test area 120 also forms an image within the fovea centralis. For example, the figure may have a circular shape, or an entire area of the test area 120 may be the figure 121.

The background area 130 corresponds to an area surrounding the fovea centralis on a person's retina. The size of the background area 130 is set so that light emitted from the background area 130 forms an image outside the fovea centralis on the human retina. For example, the size of the background area 130 is set so that the apex angle $\theta_{OUT}$ (see FIG. 1) of the cone with the background area 130 as the base and the eyes of the subject 500 as the vertex is approximately 40 degrees (see FIG. 1). The rod cells are mostly located around ±20 degrees when the fovea centralis is the center (0 degrees) of the visual field. Therefore, the background area 130 should be set so that the apex angle $\theta_{OUT}$ is 40 degrees or more so that light emitted from the background area 130 forms an image on the rod cells. The figure of the background area 130 is not limited to circular. If the display screen of the display 100 is rectangular, all areas of the display screen other than the test area 120 may be the background area 130.

On the fovea centralis of the human retina, M cone cells, which are sensitive to green light, and L cone cells, which are sensitive to red light are located. The fovea centralis contains few S cone cells and rod cells. On the other hand, S, M, and L cone cells and rod cells are located in the area outside the fovea centralis.

Human eyesight is higher when the fovea centralis is used. When a human see objects, images, or letters, he/she recognize the figure and color of the observed object mainly using M and L cone cells located in the fovea centralis. That is, the human can recognize colors using only M and L cone cells. In addition, people recognize not only color but also luminance by using S and M cone cells and rod cells around the fovea centralis. Therefore, it is possible to test a human's color vision characteristics by performing a visual test on the M and L cone cells in the fovea centralis. In addition, the degree of photosensitivity can be tested by testing the S cone and rod cells located in and around the fovea centralis.

The figure 121 in the test area 120 is an area used for the color vision test by the M and L cone cells in the fovea centralis and has a chromatic color. In addition, the background area 130 is achromatic color in this embodiment. That is, in the background area 130, the magnitudes of the R, G, and B components in a RGB color space are the same. This is because if a chromatic color is used in the background area 130, the color of the background area 130 may affect the color vision test using the test area 120. The color of the background area 130 must include a color to which the rod cells are sensitive. For example, the color of the background area 130 is a color other than black (i.e., zero magnitude of the R, G, and B components). The color of the background area 130 may also be white. The background area 130 need not be a uniform color throughout, but may include areas of relatively low or high luminance.

The test image set contains a plurality of the test images 110 that differ from each other in the color of the figure 121 or the color of the background area 130. As an example, in this embodiment, the test image set includes 345 types of different test images 110 with different colors from each other. Specifically, for the background area 130, the test images 110B include 115 types test images 110B with different blue component colors, 115 types test images 110R with different red component colors, and 115 types test images 110G with different green component colors. The test image 110B is a test image for testing the sensitivity of the subject 500 to blue light. Test image 110R is a test image for testing the sensitivity of the subject 500 to red light. Test image 110G is a test image for testing the sensitivity of the subject 500 to green light.

The colors of the plurality of test images 110B, where the colors of the background area 130 are different from each other, are set in such a manner that, for example, luminance of the background area 130 varies in 5% increments or 10% increments. The colors of the plurality of test images 110G, where the colors of the background area 130 are different from each other, are set in such a manner that, for example, the luminance of the background area 130 varies in 5% increments or 10% increments. The colors of the plurality of test images 110R, where the colors of the background area 130 are different from each other, are set in such a manner that, for example, luminance of the background area 130 varies in 5% increments or 10% increments. The increments of the luminance of the background area 130 are not limited to 5% or 10%.

Since the test image 110 is displayed on the display 100, the test image 110 is gamma-corrected according to a gamma value of the display 100 before being displayed. In detail, when an input value of an image signal input to the display 100 is x, an output value (luminance) is y, and the gamma value of the display 100 is γ, $y=x^{\gamma}$ is valid. Therefore, the input value for changing the luminance y on the display 100 is calculated by $x=y^{1/\gamma}$. In this embodiment, the RGB components of the test image 110 are the input values (xR, xG, xB) to this display 100, and each input value is represented by 256 shading from 0 to 255. The RGB components of the background area 130 are the input values ($xR_{BG}$, $xG_{BG}$, $xB_{BG}$) to the display 100, and each input value is represented by 256 shading from 0 to 255.

Table 1 shows the input values ($xR_{BG}$, $xG_{BG}$, $xB_{BG}$) of the background area 130 and the input values (xR, xG, xB) of the figure 121 of the 115 types of the test images 110B.

TABLE 1

| | Luminance of Background Area [%] | | | | | |
|---|---|---|---|---|---|---|
| Difference of Blue Component of Figure | 100% | 90% | 80% | 70% | 60% | 50% |
| | Input Value of Background Area | | | | | |
| from Background Area [%] | (255, 255, 255) | (243, 243, 243) | (230, 230, 230) | (217, 217, 217) | (202, 202, 202) | (186, 186, 186) |
| | Input Value of Figure | | | | | |
| −60% | (255, 255, 168) | (243, 243, 160) | (230, 230, 152) | (217, 217, 143) | (202, 202, 133) | (186, 186, 123) |
| −50% | (255, 255, 186) | (243, 243, 177) | (230, 230, 168) | (217, 217, 158) | (202, 202, 148) | (186, 186, 136) |
| −40% | (255, 255, 202) | (243, 243, 193) | (230, 230, 183) | (217, 217, 172) | (202, 202, 160) | (186, 186, 148) |
| −30% | (255, 255, 217) | (243, 243, 207) | (230, 230, 196) | (217, 217, 184) | (202, 202, 172) | (186, 186, 158) |
| −20% | (255, 255, 230) | (243, 243, 220) | (230, 230, 208) | (217, 217, 196) | (202, 202, 183) | (186, 186, 168) |
| −10% | (255, 255, 243) | (243, 243, 232) | (230, 230, 220) | (217, 217, 207) | (202, 202, 193) | (186, 186, 177) |
| +10% | — | (243, 243, 254) | (230, 230, 241) | (217, 217, 226) | (202, 202, 211) | (186, 186, 194) |
| +20% | — | — | (230, 230, 250) | (217, 217, 236) | (202, 202, 220) | (186, 186, 202) |

TABLE 1-continued

| | | | | | | |
|---|---|---|---|---|---|---|
| +30% | — | — | — | (217, 217, 244) | (202, 202, 228) | (186, 186, 210) |
| +40% | — | — | — | (217, 217, 253) | (202, 202, 236) | (186, 186, 217) |
| +50% | — | — | — | — | (202, 202, 243) | (186, 186, 224) |
| +60% | — | — | — | — | (202, 202, 250) | (186, 186, 230) |

| Difference of Blue Component of Figure from Background Area [%] | Luminance of Background Area [%] | | | | |
|---|---|---|---|---|---|
| | 40% | 30% | 20% | 10% | 5% |
| | Input Value of Background Area | | | | |
| | (168, 168, 168) | (148, 148, 148) | (123, 123, 123) | (90, 90, 90) | (65, 65, 65) |
| | Input Value of Figure | | | | |
| −60% | (168, 168, 111) | (148, 148, 97) | (123, 123, 81) | (90, 90, 59) | (65, 65, 43) |
| −50% | (168, 168, 123) | (148, 148, 108) | (123, 123, 90) | (90, 90, 65) | (65, 65, 48) |
| −40% | (168, 168, 133) | (148, 148, 117) | (123, 123, 97) | (90, 90, 71) | (65, 65, 52) |
| −30% | (168, 168, 143) | (148, 148, 125) | (123, 123, 104) | (90, 90, 76) | (65, 65, 56) |
| −20% | (168, 168, 152) | (148, 148, 133) | (123, 123, 111) | (90, 90, 81) | (65, 65, 59) |
| −10% | (168, 168, 160) | (148, 148, 141) | (123, 123, 117) | (90, 90, 85) | (65, 65, 62) |
| +10% | (168, 168, 176) | (148, 148, 154) | (123, 123, 128) | (90, 90, 93) | (65, 65, 68) |
| +20% | (168, 168, 183) | (148, 148, 160) | (123, 123, 133) | (90, 90, 97) | (65, 65, 71) |
| +30% | (168, 168, 189) | (148, 148, 166) | (123, 123, 138) | (90, 90, 101) | (65, 65, 74) |
| +40% | (168, 168, 196) | (148, 148, 172) | (123, 123, 143) | (90, 90, 104) | (65, 65, 76) |
| +50% | (168, 168, 202) | (148, 148, 177) | (123, 123, 148) | (90, 90, 108) | (65, 65, 79) |
| +60% | (168, 168, 208) | (148, 148, 183) | (123, 123, 152) | (90, 90, 111) | (65, 65, 81) |

The "Luminance of Background Area [%]" in Table 1 represents the luminance in a case where the luminance is 100% when the background area 130 is white (i.e., the input value is (255, 255, 255)). The "Color Components of Background Area" represent the input values ($xR_{BG}$, $xG_{BG}$, $xB_{BG}$) at the luminance [%] of the respective background area 130. In this embodiment, there are 11 types of background areas 130B (5%, 10%, 20%, 30%, 40%, 50%, 60%, 70%, 80%, 90%, and 100%). Since the background area 130B is achromatic in this embodiment, the RGB color components have the same magnitude in each background area 130.

The "Difference of Blue Component of Figure from Background Area [%]" in the table represents the luminance of the blue component of the figure 121 as the difference from the luminance of the blue component of the background area 130, when the luminance of the blue component of the background area 130 is 100%. In this embodiment, there are 12 types of differences [%] of the blue component of figure 121 from the background area 130, ranging from −60% to +60% in 10% increments. In this embodiment, the magnitude of the red and green components of the background area 130 are the same as the magnitude of the red and green components of the figure 121, respectively. Therefore, if the difference of the blue component of the figure 121 from the background area 130 is 0%, it is not included in the test image 110B because the figure 121 and the background area 130 are the same color.

The test image 110B is a combination of the background area 130 and the FIG. 121 with the input values listed in the same column as the background area 130. For example, there are six types of test images 110B in which the input value of the background area 130 is (255, 255, 255), and the red and green components of the figure 121 of these six types of test images 110B are the same magnitude as the red and green components of the background area 130, respectively (i.e., 255). The blue input values of the figures 121 in these six test images 110B are set to vary in luminance from −60% to −10% in 10% increments relative to the blue input values of the background area 130, respectively. The magnitudes of the blue input values of the figure 121 of the six types of test images 110B, where the input value of the background area 130 is (255, 255, 255), are 168, 186, 202, 217, 230, and 243, respectively.

In Table 1, when the input value of the background area 130 is (255, 255, 255), the reason why the input value of the figure 121 with the difference [%] of the blue component from the background area 130 of +10% or more is not listed is because the maximum blue input value for the figure 121 is 255. Similarly, in the cases where the color components of the background area 130 are (243, 243, 243), (230, 230, 230), and (217, 217, 217), there are no cases listed where the input value of blue exceeds 255.

When the difference [%] of the blue component of figure 121 from the background area 130 is positive (+10% to +60), figure 121 has a bluish color because the magnitude of the blue component is larger than the red and green color components. The larger the difference [%] of the blue component from the background area 130, the stronger the blue tint becomes, and the color difference between the figure 121 and the background area 130 becomes clearer. On the other hand, when the difference [%] of the blue component of the figure 121 from the background area 130 is negative (−10% to −60), the red and green color components are larger than the blue component, so the figure 121 becomes a color with a yellow tint (a color with a strong green and red tints). The smaller the difference [%] of the blue component from the background area 130, the stronger the yellowish tint becomes, and the color difference between the figure 121 and the background area 130 becomes clearer.

A subject with normal color vision characteristics can easily recognize the color difference between the figure 121 and the background area 130 even when the absolute value of the difference [%] from the background area 130 of the blue component is small. On the other hand, for a subject with relatively low sensitivity to blue light to recognize the color difference between the figure 121 and the background area 130, the absolute value of the difference [%] of the blue component from the background area 130 need to be large. For example, the subject with normal color vision characteristics can recognize the figure 121 in the background area 130 if the absolute value of the difference [%] of the blue component from the background area 130 is 30% or more (i.e., −30% or less or +30% or more). On the other hand, the subject with low sensitivity to blue light cannot recognize the figure 121 even when the absolute value of the difference [%] from the background area 130 of the blue component is 30%, and can recognize the figure 121 within the background area 130 when the absolute value of the difference

[%] from the background area 130 of the blue component is, for example, 40% or more. If the subject has photosensitivity, the figure 121 within the background area 130 can be recognized even when the absolute value of the difference [%] of the blue component from the background area 130 is less than 30% because the subject has high sensitivity to blue light.

In general, the higher the luminance of the background area 130 and the figure 121, the easier it is for the subject with normal color vision characteristics to recognize color differences in the background area 130 and the figure 121. On the other hand, if the subject has photosensitivity with high sensitivity to blue light, the higher luminance of the background area 130 and the figure 121 will cause the subject to feel dazzled by the test image 110B. Therefore, for the subject with photosensitivity, it is easier to recognize the color difference between the background area 130 and the figure 121 when the "Luminance of Background Area [%]" is lower than 100%. Even if the subject has photosensitivity, if the luminance [%] of the background area 130 is reduced, the subject may have difficulty recognizing the figure 121 in the background area 130 when the absolute value of the difference [%] of the blue component from the background area 130 is less than 30%. In this case, if the luminance [%] of the background area 130 is decreased, the absolute value of the difference [%] from the background area 130 of the blue component must be changed to 30% or higher in order for the subject to be able to recognize the figure 121 in the background area 130.

Thus, depending on what color vision characteristics the subject has, the conditions under which the subject can recognize the difference in color of the background area 130 and the figure 121 (in other words, can recognize the figure 121 in the background area 130) are different. Therefore, by using a plurality of test images 110B with different luminances (i.e., luminances of background area 130 and figure 121) and different colors of the figure 121 relative to background area 130, it is possible to determine what kind of color vision characteristics the subject has for blue light. Table 1 shows examples of the test images 110B where the difference [%] of the blue component of figure 121 from the background area 130 ranges from −60% to +60%, but the test images 110B are not limited to these. For example, the test images 110B in which the difference [%] from the background area 130 of the blue component of the figure 121 is smaller than −60%, and the test images 110B in which the difference [%] from the background area 130 of the blue component of the figure 121 is larger than +60% may be provided.

Tables 2 and 3 show the input values ($xR_{BG}$, $xG_{BG}$, $xB_{BG}$) of the background area 130 and the input values (xR, xG, xB) of the figure 121 in test images 110R when the red component of the figure 121 is different with respect to the background area 130 and in test images 110G when the green component of the figure 121 is different with respect to the background area 130, respectively.

TABLE 2

| Difference of Green Component of Figure from Background Area [%] | Luminance of Background Area [%] 100% | 90% | 80% | 70% | 60% | 50% |
|---|---|---|---|---|---|---|
| Input Value of Background Area | (255, 255, 255) | (243, 243, 243) | (230, 230, 230) | (217, 217, 217) | (202, 202, 202) | (186, 186, 186) |
| | Input Value of Figure | | | | | |
| −60% | (255, 168, 255) | (243, 160, 243) | (230, 152, 230) | (217, 143, 217) | (202, 133, 202) | (186, 123, 186) |
| −50% | (255, 186, 255) | (243, 177, 243) | (230, 168, 230) | (217, 158, 217) | (202, 148, 202) | (186, 136, 186) |
| −40% | (255, 202, 255) | (243, 193, 243) | (230, 183, 230) | (217, 172, 217) | (202, 160, 202) | (186, 148, 186) |
| −30% | (255, 217, 255) | (243, 207, 243) | (230, 196, 230) | (217, 184, 217) | (202, 172, 202) | (186, 158, 186) |
| −20% | (255, 230, 255) | (243, 220, 243) | (230, 208, 230) | (217, 196, 217) | (202, 183, 202) | (186, 168, 186) |
| −10% | (255, 243, 255) | (243, 232, 243) | (230, 220, 230) | (217, 207, 217) | (202, 193, 202) | (186, 177, 186) |
| +10% | — | (243, 254, 243) | (230, 241, 230) | (217, 226, 217) | (202, 211, 202) | (186, 194, 186) |
| +20% | — | — | (230, 250, 230) | (217, 236, 217) | (202, 220, 202) | (186, 202, 186) |
| +30% | — | — | — | (217, 244, 217) | (202, 228, 202) | (186, 210, 186) |
| +40% | — | — | — | (217, 253, 217) | (202, 236, 202) | (186, 217, 186) |
| +50% | — | — | — | — | (202, 243, 202) | (186, 224, 186) |
| +60% | — | — | — | — | (202, 250, 202) | (186, 230, 186) |

| Difference of Green Component of Figure from Background Area [%] | Luminance of Background Area [%] 40% | 30% | 20% | 10% | 5% |
|---|---|---|---|---|---|
| Input Value of Background Area | (168, 168, 168) | (148, 148, 148) | (123, 123, 123) | (90, 90, 90) | (65, 65, 65) |
| | Input Value of Figure | | | | |
| −60% | (168, 111, 168) | (148, 97, 148) | (123, 81, 123) | (90, 59, 90) | (65, 43, 65) |
| −50% | (168, 123, 168) | (148, 108, 148) | (123, 90, 123) | (90, 65, 90) | (65, 48, 65) |
| −40% | (168, 133, 168) | (148, 117, 148) | (123, 97, 123) | (90, 71, 90) | (65, 52, 65) |
| −30% | (168, 143, 168) | (148, 125, 148) | (123, 104, 123) | (90, 76, 90) | (65, 56, 65) |
| −20% | (168, 152, 168) | (148, 133, 148) | (123, 111, 123) | (90, 81, 90) | (65, 59, 65) |
| −10% | (168, 160, 168) | (148, 141, 148) | (123, 117, 123) | (90, 85, 90) | (65, 62, 65) |
| +10% | (168, 176, 168) | (148, 154, 148) | (123, 128, 123) | (90, 93, 90) | (65, 68, 65) |
| +20% | (168, 183, 168) | (148, 160, 148) | (123, 133, 123) | (90, 97, 90) | (65, 71, 65) |
| +30% | (168, 189, 168) | (148, 166, 148) | (123, 138, 123) | (90, 101, 90) | (65, 74, 65) |
| +40% | (168, 196, 168) | (148, 172, 148) | (123, 143, 123) | (90, 104, 90) | (65, 76, 65) |
| +50% | (168, 202, 168) | (148, 177, 148) | (123, 148, 123) | (90, 108, 90) | (65, 79, 65) |
| +60% | (168, 208, 168) | (148, 183, 148) | (123, 152, 123) | (90, 111, 90) | (65, 81, 65) |

TABLE 3

| Difference of Red Component of Figure from Background Area [%] | Luminance of Background Area [%] | | | | | |
|---|---|---|---|---|---|---|
| | 100% | 90% | 80% | 70% | 60% | 50% |
| | Input Value of Background Area | | | | | |
| | (255, 255, 255) | (243, 243, 243) | (230, 230, 230) | (217, 217, 217) | (202, 202, 202) | (186, 186, 186) |
| | Input Value of Figure | | | | | |
| −60% | (168, 255, 255) | (160, 243, 243) | (152, 230, 230) | (143, 217, 217) | (133, 202, 202) | (123, 186, 186) |
| −50% | (186, 255, 255) | (177, 243, 243) | (168, 230, 230) | (158, 217, 217) | (148, 202, 202) | (136, 186, 186) |
| −40% | (202, 255, 255) | (193, 243, 243) | (183, 230, 230) | (172, 217, 217) | (160, 202, 202) | (148, 186, 186) |
| −30% | (217, 255, 255) | (207, 243, 243) | (196, 230, 230) | (184, 217, 217) | (172, 202, 202) | (158, 186, 186) |
| −20% | (230, 255, 255) | (220, 243, 243) | (208, 230, 230) | (196, 217, 217) | (183, 202, 202) | (168, 186, 186) |
| −10% | (243, 255, 255) | (232, 243, 243) | (220, 230, 230) | (207, 217, 217) | (193, 202, 202) | (177, 186, 186) |
| +10% | — | (254, 243, 243) | (241, 230, 230) | (226, 217, 217) | (211, 202, 202) | (194, 186, 186) |
| +20% | — | — | (250, 230, 230) | (236, 217, 217) | (220, 202, 202) | (202, 186, 186) |
| +30% | — | — | — | (244, 217, 217) | (228, 202, 202) | (210, 186, 186) |
| +40% | — | — | — | (253, 217, 217) | (236, 202, 202) | (217, 186, 186) |
| +50% | — | — | — | — | (243, 202, 202) | (224, 186, 186) |
| +60% | — | — | — | — | (250, 202, 202) | (230, 186, 186) |

| Difference of Red Component of Figure from Background Area [%] | Luminance of Background Area [%] | | | | |
|---|---|---|---|---|---|
| | 40% | 30% | 20% | 10% | 5% |
| | Input Value of Background Area | | | | |
| | (168, 168, 168) | (148, 148, 148) | (123, 123, 123) | (90, 90, 90) | (65, 65, 65) |
| | Input Value of Figure | | | | |
| −60% | (111, 168, 168) | (97, 148, 148) | (81, 123, 123) | (59, 90, 90) | (43, 65, 65) |
| −50% | (123, 168, 168) | (108, 148, 148) | (90, 123, 123) | (65, 90, 90) | (48, 65, 65) |
| −40% | (133, 168, 168) | (117, 148, 148) | (97, 123, 123) | (71, 90, 90) | (52, 65, 65) |
| −30% | (143, 168, 168) | (125, 148, 148) | (104, 123, 123) | (76, 90, 90) | (56, 65, 65) |
| −20% | (152, 168, 168) | (133, 148, 148) | (111, 123, 123) | (81, 90, 90) | (59, 65, 65) |
| −10% | (160, 168, 168) | (141, 148, 148) | (117, 123, 123) | (85, 90, 90) | (62, 65, 65) |
| +10% | (176, 168, 168) | (154, 148, 148) | (128, 123, 123) | (93, 90, 90) | (68, 65, 65) |
| +20% | (183, 168, 168) | (160, 148, 148) | (133, 123, 123) | (97, 90, 90) | (71, 65, 65) |
| +30% | (189, 168, 168) | (166, 148, 148) | (138, 123, 123) | (101, 90, 90) | (74, 65, 65) |
| +40% | (196, 168, 168) | (172, 148, 148) | (143, 123, 123) | (104, 90, 90) | (76, 65, 65) |
| +50% | (202, 168, 168) | (177, 148, 148) | (148, 123, 123) | (108, 90, 90) | (79, 65, 65) |
| +60% | (208, 168, 168) | (183, 148, 148) | (152, 123, 123) | (111, 90, 90) | (81, 65, 65) |

In the test image 110R shown in Table 2, when the difference [%] of the red component of the figure 121 from the background area 130 is positive (+10% to +60), since the red component is larger than the green and blue color components, the figure 121 has a red tint. The larger the difference [%] of the red component from the background area 130, the stronger the red tint becomes, and the color difference between the figure 121 and the background area 130 becomes clearer. On the other hand, when the difference [%] of the red component of figure 121 from the background area 130 is negative (−10% to −60), since the green and blue color components are larger than the red component, the color of figure 121 becomes cyan (i.e, a color with strong green and blue tints). The smaller the difference [%] of the red component from the background area 130, the clearer the cyan color becomes and the more distinct the color difference between the figure 121 and the background area 130.

In the test image 110G shown in Table 3, when the difference [%] of the green component of the figure 121 from the background area 130 is positive (+10% to +60%), since the green component is larger than the red and blue color components, the figure 121 has a green tint color. The larger the difference [%] of the green component from the background area 130, the stronger the green tint becomes, and the color difference between the figure 121 and the background area 130 becomes clearer. On the other hand, when the difference [%] of the green component of figure 121 from the background area 130 is negative (−10% to −60), since the red and blue color components are larger than the green component, the color of figure 121 is magenta (i.e., a color with strong red and blue tints). The smaller the difference [%] of the green component from the background area 130, the clearer the magenta color becomes and the clearer the color difference between the figure 121 and the background area 130.

Similarly to the test image 110B, in the test image 110R and the test image 110G, the subject 500 with normal color vision characteristics can easily recognize the color difference between the figure 121 and the background area 130 even when the absolute values of the difference [%] of the red component of the figure 121 from the background area 130 and the difference [%] of the green component from the background area 130 are small (that is, the colors of figure 121 and background area 130), it is easy to recognize the difference in color between the figure 121 and the background area 130. On the other hand, in order for the subject 500 with relatively low sensitivity to red or green light to recognize the color difference between the figure 121 and the background area 130, the absolute values of the difference [%] of the red component of the figure 121 from the background area 130 and the difference [%] of the green component from the background area 130 must be large. For example, the subject 500 with normal color vision characteristics can recognize the figure 121 located in the background area 130 when the absolute value of the difference [%] of the red component of the figure 121 from the background area 130 or the difference [%] of the green component from the background area 130 is 30% or more (i.e., −30% or less or +30% or more). On the other hand, the subject 500 with low sensitivity to red or green light cannot recognize the figure 121 even if the absolute value of the difference [%] of the red component of the figure 121 from the background area 130 or the difference [%] of the green component from the background area 130 is 30%. For example, the subject 500 can recognize the figure 121 when the absolute value of the difference [%] from the background area 130 of the red component is 50% or more.

In general, the higher the luminance of the background area 130 and the figure 121, the easier it is for the subject with normal color vision characteristics to recognize color differences between the background area 130 and the figure 121. On the other hand, when the subject has photosensitivity with high sensitivity to blue light, the higher luminance of the background area 130 and the figure 121 will cause the subject to feel dazzled by the test image 110B. Therefore, for the subject with photosensitivity, it is easier to recognize the color difference between the background area 130 and the figure 121 when the "Luminance of Background Area [%]" is lower than 100%.

Thus, depending on what kind of color vision characteristics the subject has, the conditions that he/she can recognize the difference colors between the background area 130 and the figure 121 (in other words, the conditions under which he/she can recognize the FIG. 121 in the background area 130) differ. Therefore, by using multiple test images 110R and 110G that differ in luminance of the test images 110R and 110G (luminance of the background area 130 and the figure 121) and the color difference of the figure 121 with respect to the background area 130, it is possible to determine what kind of color vision characteristics the subject has for red and green light. The color vision characteristics of the subject can be determined. A table 2 shows examples of test images 110R where the difference [%] of the red component of figure 121 from the background area 130 ranges from −60% to +60%, but the test images 110R are not limited to these. For example, the test images 110R in which the difference [%] of the red component of figure 121 from the background area 130 is smaller than −60% and the test images 110R in which the difference [%] of the red component of FIG. 121 from the background area 130 is larger than +60% may be provided. A table 3 shows examples of test images 110G where the difference [%] of the green component of the FIG. 121 from the background area 130 is from −60% to +60%, but test images 110G are not limited to these. For example, the test images 110G in which the difference [%] of the green component of the figure 121 from the background area 130 is smaller than −60% and the test images 110G in which the difference [%] of the green component of the figure 121 from the background area 130 is larger than +60% may be provided.

[Test Method of Visual Characteristics]

Figure 5:
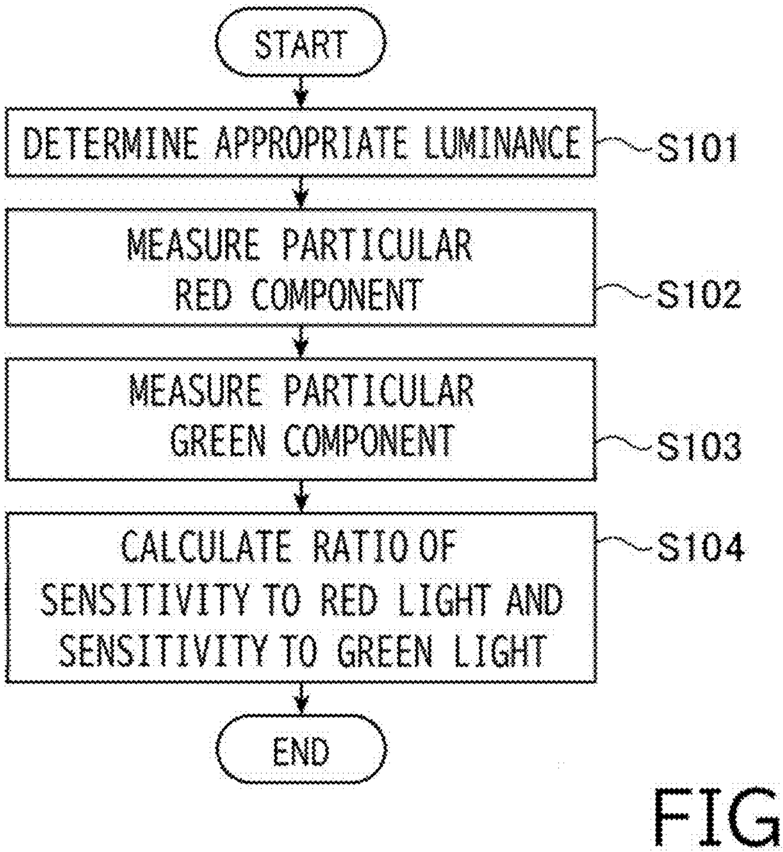
FIG. 5 shows a flowchart of the test method for visual characteristics according to aspects of the present disclosure.

Next, the test method for visual characteristics using a test system of the visual characteristics 1 including the test image 110 is described. FIG. 5 shows a flowchart of the test method for visual characteristics using the test image 110.

[Process Step S101 in FIG. 5]

In S101, an appropriate luminance $B_{CENTER}$, which is a luminance [%] of the background area 130 of the test image 110 that is appropriate for the subject 500, is determined.

In S101, at first, the test images 110B with a difference [%] of −30% from the background area 130 of the blue component of the figure 121 are sequentially displayed on the display 100 while changing the luminance [%] of the background area 130. The test images 110B to be displayed may be displayed in the order of the luminance [%] of the background area 130 from smallest or from largest. The test images 110B may be displayed in order of the luminance [%] of the background area 130 in order of decreasing luminance [%] of the background area 130, and then in order of increasing luminance [%] of the background area 130. Alternatively, the luminance [%] of the background area 130 may be changed randomly. When the luminance [%] of the background area 130 changes, the color component of the figure 121 also changes accordingly, with the blue component of the figure 121 maintained at −30% relative to the blue component of the background area 130. A time period in which one test image 110B is displayed is, for example, a time period in which the subject 500 can respond to the results of the confirmation after checking whether or not he/she feels dazzled by the test image 110B and whether or not he/she can recognize the figure 121. For example, one test image 110B is displayed for more than 1 second, after which the next test image 110B with a different luminance [%] of the background area 130 is displayed. When the figure 121 is a Landolt ring, whether or not the subject 500 can recognize the figure 121 can be confirmed by whether or not the subject 500 can see the cutout position of the Landolt ring (a right side in the example of FIG. 4).

If the subject 500 has healthy visual characteristics for blue light, the subject 500 will be able to recognize the figure 121 in the background area 130 regardless of the luminance [%] of the background area 130. If the subject 500 has photosensitivity, he/she will feel dazzled by the test image 110B when the luminance [%] of the background area 130 is high. Therefore, the subject 500 having photosensitivity will not be able to recognize the figure 121 in the test image 110B when the luminance [%] of the background area 130 is relatively high, and will be able to recognize the figure 121 in the test image 110B when the luminance [%] of the background area 130 is relatively low. On the other hand, if the subject 500 has low visual sensitivity to blue light, he/she will not be able to recognize the figure 121 in the test image 110B in which the difference [%] of the blue component of the figure 121 from the background area 130 is −30% because it is difficult to recognize changes in the blue component of the FIG. 121. Therefore, by testing whether the subject 500 can recognize the figure 121 in the background area 130, the sensitivity of the subject 500 to blue light or the difference between the sensitivity of the subject 500 to blue light and the sensitivity of a healthy human to blue light can be tested.

If the subject 500 can recognize the figure 121 in the test image 110B with a difference [%] of −30% from the background area 130 of the blue component of the figure 121, it means that the sensitivity of the subject 500 to blue light is at least as high as that of a healthy human to blue light. On the other hand, if the subject 500 is unable to recognize the figure 121 in the test image 110B in which the difference [%] of the blue component of the figure 121 from the background area 130 is −30%, it means that the sensitivity of the subject 500 to blue light is lower than that of a healthy human to blue light. In a case where the luminance [%] of the background area 130 is lower than 100%, since the subject 500 who has photosensitivity is highly sensitive to blue light, he/she will be able to recognize the figure 121 in the test image 110B even when the difference [%] of the blue component of the figure 121 from the background area 130 is greater than −30% (that is, the color of the figure 121 is closer to the color of the background area 130).

The subject 500 specifies the luminance [%] of the background area 130 that the figure 121 can be recognized while looking at the test image 110B in which the luminance [%] of the background area 130 changes. Then, a central value (or a value close to the central value) of the range of luminance [%] of the background area 130 in which the subject 500 can recognize the figure 121 is specified as the appropriate luminance $B_{CENTER}$. The appropriate luminance $B_{CENTER}$ may be the value with the highest luminance in the range of luminance [%] of the background area 130 that the subject 500 can recognize the figure 121. If the subject 500 can recognize the figure 121 regardless of the luminance [%] of the background area 130, the appropriate luminance $B_{CENTER}$ may be 100%. The subject 500 being able to recognize the figure 121 is an example of the first test condition.

If the subject 500 cannot recognize the figure 121 in the test image 110B with a difference [%] of −30% from the background area 130 of the blue component of the figure 121, the test image 110B with a difference [%] of −40% from the background area 130 of the blue component of the figure 121 is displayed. The subject 500 is then tested to see if he/she can recognize the figure 121 in the background area 130 of the displayed test image 110B. At this time, the luminance [%] of the background area 130 of the displayed test image 110B may be sequentially changed. If the subject 500 cannot recognize the figure 121 in the test image 110B with a difference [%] of −40% from the background area 130 of the blue component of the figure 121, the test image 110B is displayed with the difference [%] of the blue component of the figure 121 from the background area 130 set lower. In this way, the difference [%] of the blue component of the figure 121 from the background area 130 is changed until the subject 500 can recognize the figure 121. Thus, the sensitivity of the subject 500 to blue light can be tested to see how much lower the sensitivity of the subject 500 to blue light is than that of a healthy human to blue light. If the subject 500 can recognize the figure 121 in the test image 110B with a difference [%] of −30% from the background area 130 of the blue component of the figure 121, the test image 110B with the difference [%] of the blue component of the FIG. 121 from the background area 130 is closer to 0 (for example, −20% or −10%) may be displayed to test whether the subject 500 can recognize the figure 121.

In the process of S101, the test image 110B with a difference [%] of −30% from the background area 130 of the blue component of the figure 121 is initially displayed, and the difference [%] of the blue component of the figure 121 from the background area 130 is changed to lower according to the test results, but the embodiment of the present disclosure is not limited to these processes. For example, the test image 110B with a difference [%] of +30% from the background area 130 of the blue component of the figure 121 is initially displayed first, and the difference [%] of the displayed test image 110B from the background area 130 of the blue component of the figure 121 may be changed to a higher value according to the test results. In addition, the test image 110B is initially displayed with a small absolute value (e.g., −10% or +10%) of the difference [%] from the background area 130 of the blue component of the figure 121 of the test image 110B, and according to the test results, the absolute value of the difference [%] between the two may be changed in such a manner that the absolute value of the difference [%] is increased. Alternatively, the test image 110B may be initially displayed with the absolute value of the difference [%] of the blue component of the figure 121 from the background area 130 of the blue component of the figure 121 being large (e.g., −60% or +60%), and according to the test results, the absolute value of the difference [%] of the blue component of the figure 121 of the displayed test image 110B from the background area 130 may be changed in such a manner that the absolute value of the difference [%] from the background area is smaller.

[Process Step S102 in FIG. 5]

In S102, the particular red component $R_{VALUE}$, which is the red component that enables the subject 500 to recognize the figure 121 in the background area 130 of the test image 110R, is measured. Specifically, the difference [%] from the background area 130 of the red component that enables the subject 500 to recognize the figure 121 in the background area 130 is identified. Being able to recognize the figure 121 in the background area 130 specifically means being able to recognize the difference in color between the figure 121 and the background area 130 and being able to identify the figure 121 in the background area 130. The subject 500 being able to recognize the figure 121 is an example of the second test condition.

In S102, the test image 110R is sequentially displayed on the display 100 with the difference [%] of the red component of the figure 121 from the background area 130 changing from −10% to −60%. At this time, the luminance [%] of the background area 130 of the test image 110R is set to the appropriate luminance $B_{CENTER}$ specified in S101.

In the test image 110R, where the difference [%] of the red component of the FIG. 121 from the background area 130 is −10%, the magnitude of the red component of figure 121 is 10% smaller than that of the green component. As the red component of the figure 121 becomes smaller (as the difference [%] of the red component from the background area 130 changes toward −60%), the difference between the red and green components of the figure 121 becomes larger, and the color difference between the figure 121 and the background area 130 becomes larger. If the subject 500 has healthy visual characteristics for red and green light, the subject 500 will be able to recognize the figure 121 in the background area 130 in the test image 110R where the difference [%] of the red component of the figure 121 from the background area 130 is −30% or less. On the other hand, if the subject 500 has relatively low sensitivity to red light, he/she will not be able to recognize the figure 121 in the test image 110R where the difference [%] of the red component of the figure 121 from the background area 130 is −30%. Therefore, by testing whether the subject 500 can recognize the figure 121 in the background area 130, the sensitivity of the subject 500 to red light, or the difference between the sensitivity of the subject 500 to red light and the sensitivity of a healthy human to red light, can be tested. In other words, the sensitivity of the L cone cells of the subject 500, or the difference between the sensitivity of the L cone cells of the subject 500 and the sensitivity of the L cone cells of a healthy human can be tested.

If the subject 500 can recognize the figure 121 of the test image 110R with the difference [%] of the red component of the figure 121 from the background area 130 is −30%, it means that the sensitivity of the subject 500 to red light is at least as high as that of a healthy human to red light. On the other hand, if the subject 500 cannot recognize the figure 121 of the test image 110R with a light color component of −30% of the figure 121, it means that the sensitivity of the subject 500 to red light is lower than that of a healthy human to red light.

If the subject 500 cannot recognize the figure 121 in the test image 110R with a difference [%] of −30% from the background area 130 of the red component of the figure 121, the difference [%] of the red component of the figure 121 in the test image 110R from the background area 130 is −40%. Then, it is tested whether the subject 500 can recognize the figure 121 in the background area 130 of the displayed test image 110R. At this time, the luminance [%] of the background area 130 of the displayed test image 110R may be sequentially changed. If the subject 500 cannot recognize the figure 121 in the test image 110R with the difference [%] of the red component of the figure 121 from the background area 130 is −40%, the test image 110R is displayed with the red component of the figure 121 set even lower. In this way, the test image 110R is sequentially displayed on the display 100 while changing the difference [%] of the red component of the figure 121 from the background area 130 from −10% to −60%, the difference [%] from the background area 130 of the red component with the smallest absolute value is identified among the differences [%] from the background area 130 of the red component that the subject 500 can recognize the figure 121. In other words, among the test images 110R that the subject 500 can recognize the figure 121, the one in which the colors of the background area 130 and the figure 121 are closest is identified. This allows the test to test the extent to which the sensitivity of the subject 500 to red light differs from that of a healthy human to red light.

In the process of S102, the test image 110R with a difference [%] of −10% from the background area 130 of the red component of the figure 121 is initially displayed, and the difference [%] of the red component of the figure 121 from the background area 130 is changed to lower according to the test results, but the embodiment of the present disclosure is not limited to the processes. For example, the test image 110R with the difference [%] of the red component of the figure 121 from the background area 130 of the red component of the FIG. 121 is +10% may be displayed at first, and the difference [%] of the displayed test image 110R from the background area 130 of the red component of the figure 121 may be changed to a higher value according to the test results. Alternatively, the test image 110R may be initially displayed with the absolute value of the red component of the figure 121 large (e.g., −60% or +60%), and according to the test results, the absolute value of the difference [%] of the red component of the figure 121 of the displayed test image 110R from the background area 130 of the background area 130 may be changed smaller.

[Process Step S103 in FIG. 5]

In S103, the particular green component $G_{VALUE}$, which is the green component that enables the subject 500 to recognize the figure 121 in the background area 130 of the test image 110G, is measured. Specifically, in S103, the test image 110G is sequentially displayed on the display 100 with the difference [%] of the green component of the figure 121 from the background area 130 changing from −10% to −60%. At this time, the luminance [%] of the background area 130 of the test image 110R is set to the appropriate luminance $B_{CENTER}$ identified in S101.

In S103, similar to the test in S102, whether the subject 500 can recognize the FIG. 121 in the background area 130 of the test image 110G is tested. Specifically, whether the subject 500 can recognize the difference in color between the figure 121 and the background area 130, and whether the subject 500 can identify form of the figure 121.

The test method in S103 is the same as that in S102, except that the test image 110G is used instead of the test image 110R and that the difference [%] from the background area 130 of the green component is changed instead of the difference [%] of the red component of the figure 121 from the background area 130. Specifically, the test image 110G is sequentially displayed on the display 100 while the difference [%] from the background area 130 of the green component of the figure 121 is changed from −10% to −60%, and the background area of the green component where the subject 500 can recognize the figure 121, and the difference [%] from the background area 130 of the green component with the smallest absolute value is identified among the differences [%] from the background area 130 of the green component that the subject 500 can recognize the figure 121. With this test, it is possible to test the sensitivity of the subject 500 to green light, or the difference between the sensitivity of the subject 500 to green light and the sensitivity of a healthy human to green light. In other words, the sensitivity of the M cone cells of the subject 500 or the difference between the sensitivity of the M cone cells of the subject 500 and the sensitivity of the M cone cells of a healthy human can be tested.

With the above processes from S101 to S103, the sensitivity of the subject to each of the RGB lights is tested.

In the example shown in FIG. 5, both the sensitivity of the subject 500 to red light and the sensitivity to green light were tested in S102 and S103, but the processes according to this embodiment are not limited to these processes. For example, if it is known in advance that the subject 500 has low sensitivity to either green light or red light, only the test using the test image 110 that changes the less sensitive color (either S102 or S103) may be performed. For example, if the subject 500 has the first type of color weakness with low sensitivity to red light, the test of S102 may be performed and the test of S103 may be omitted. Alternatively, if the subject 500 has a second type of color weakness with low sensitivity to green, the test of S103 may be performed and the test of S102 may be omitted.

If only a degree of photosensitivity of the subject 500 is to be tested, only S101 may be performed. The degree of photosensitivity is tested by measuring which luminance [%] of the background area 130 the subject 500 feels dazzled. Therefore, when testing the degree of photosensitivity, it is not necessary to use the test image 110B, but the test image 110R or the test image 110G may be used.

[Process Step S104 in FIG. 5]

In S104, the ratio of the sensitivity of the subject 500 to red light and the sensitivity of the subject 500 green light is calculated using the particular red component $R_{VALUE}$ and the particular green component $G_{VALUE}$ identified in S102 and S103.

If the absolute value of the particular red component $R_{VALUE}$ is greater than the absolute value of the particular green component $G_{VALUE}$, the sensitivity of the subject 500 to red light is less than the sensitivity to green light. In this case, the ratio of sensitivity is calculated as $|G_{VALUE}/R_{VALUE}|$ (absolute value of $G_{VALUE}/R_{VALUE}$). On the other hand, if the absolute value of the particular red component $R_{VALUE}$ is smaller than the absolute value of the particular green component $G_{VALUE}$, the sensitivity of the subject 500 to red light is greater than the sensitivity to green light. In this case, the ratio of sensitivity is calculated as $|R_{VVALUE}/G_{VALUE}|$ (absolute value of $R_{VALUE}/G_{VALUE}$). The calculated ratio of sensitivity is used to determine the characteristics of the correction filter that corrects the visual characteristics of the subject 500.

[Correction Filter]

Once the visual characteristics of the subject 500 are tested by the visual testing method shown in FIG. 5, the test results are used to make a correction filter that corrects the visual characteristics of the subject 500. The correction filter may be any one that changes the transmission spectrum, and there is no particular limitation on the material or the principle of changing the transmission spectrum. The correction filter is, for example, worn by the subject 500 like a pair of glasses. However, a form of the correction filter is not particularly limited. The correction filter may be in the form of contact lenses or may be attached to a display such as a television or monitor.

Figure 6:
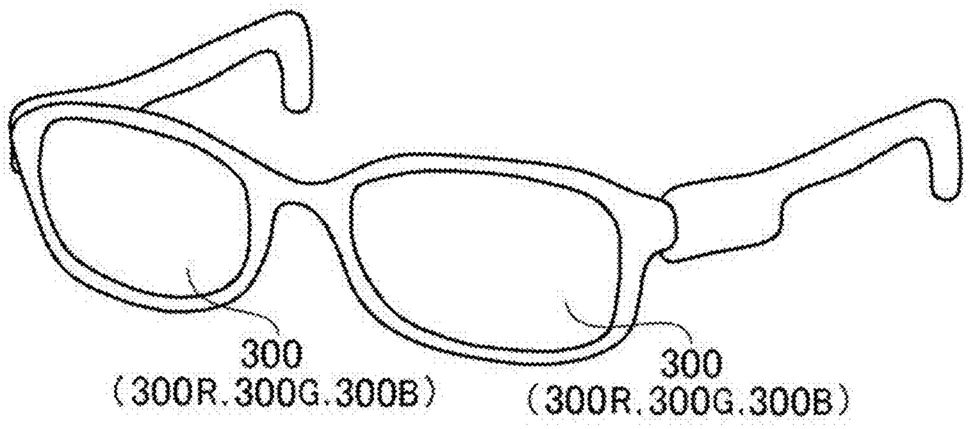
FIG. 6 shows an example of a correction filter according to aspects of the present disclosure.

FIG. 6 shows an example of a glasses-figured correction filter 300. The correction filter 300 includes, for example, a filter 300B for light in the blue region, a filter 300G for light in the green region, and a filter 300R for light in the red region. Each filter 300B, 300G, and 300R has bandwidths $B_B$, $B_G$, and $B_R$, respectively, that change the transmittance of light.

The filter 300B changes the transmittance of light in the blue region (in other words, it absorbs or reflects part of the blue light), but allows green and red lights to be transmitted as they are (in other words, it has low absorption and reflection for green and red lights). The filter 300G changes the transmittance of light in the green region (in other words, absorbs or reflects some of the green light), but allows blue and red lights to be transmitted as they are (in other words, it has low absorption or reflectance for blue and red lights). The filter 300R changes the transmittance of light in the red region (in other words, it absorbs or reflects some of the red light), but allows green and blue lights to be transmitted as they are (in other words, it has low absorption or reflectance for green and blue lights). Therefore, by combining the three filters 300B, 300G, and 300R, the transmittance to light in the three RGB wavelength bands can be adjusted individually.

Figure 7A:
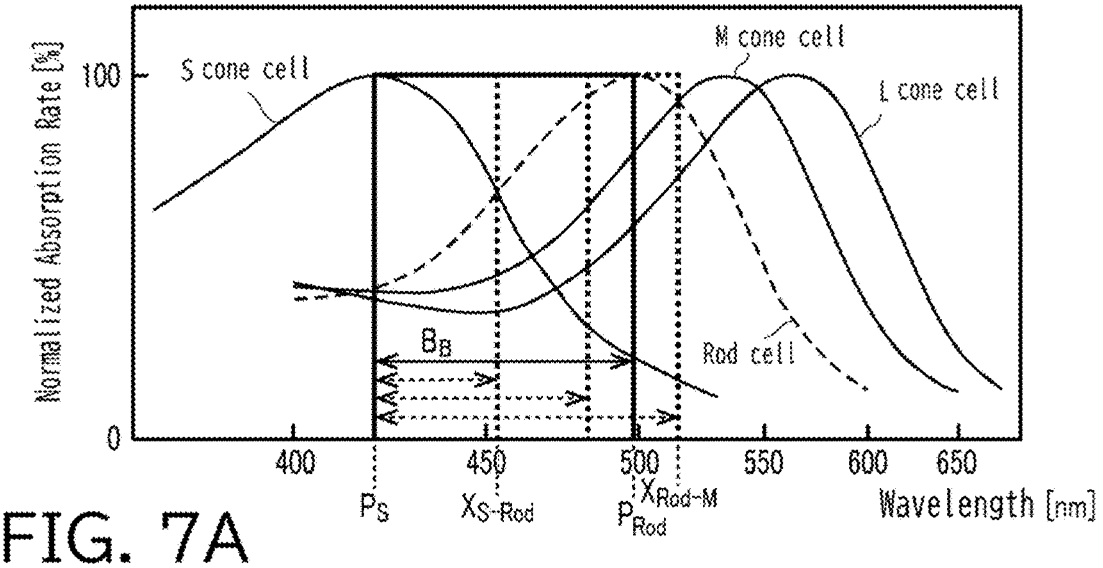
FIGS. 7A-7C show a bandwidths of correction filters according to aspects of the present disclosure.
Figure 7B:
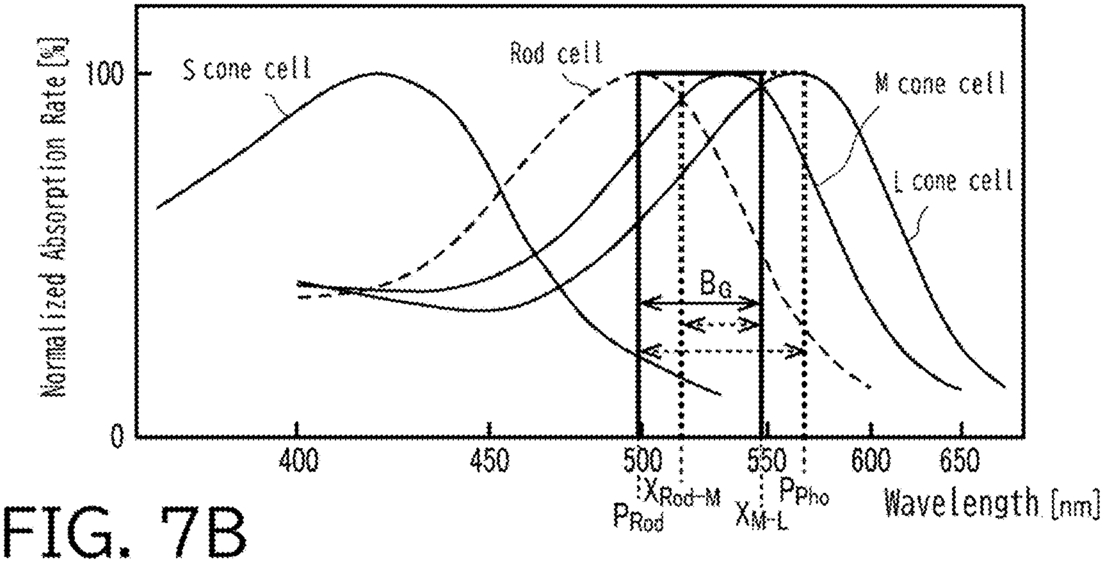
Figure 7C:
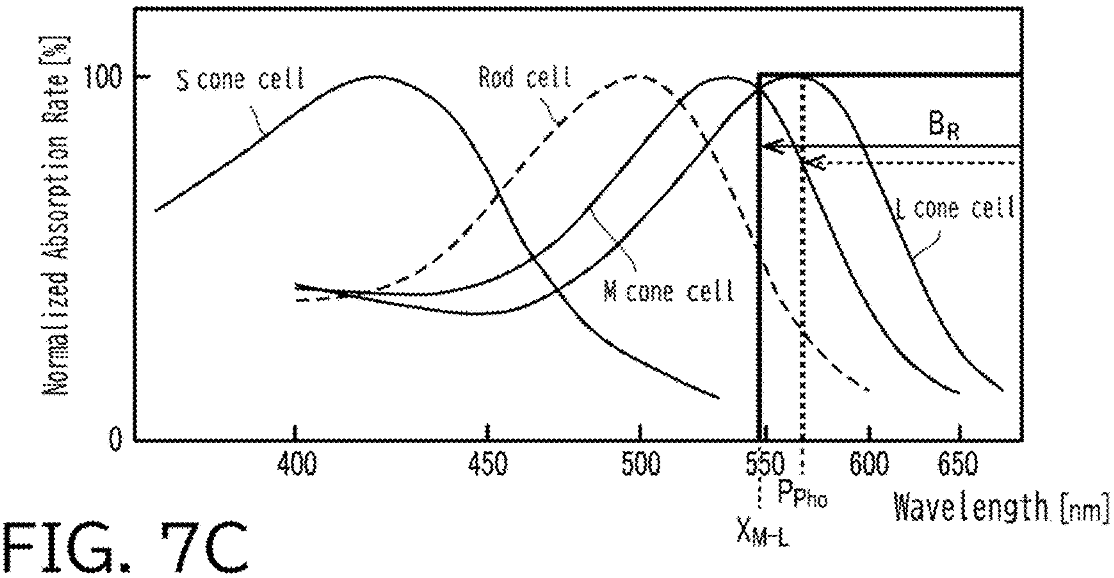

FIGS. 7A-7C show the bandwidths $B_B$, $B_G$, and $B_R$ of the three filters 300B, 300G, and 300R in which the transmittances of lights can be changed, respectively. The horizontal axes in FIGS. 7A-7C shows the wavelength of light, and the vertical axes shows the normalized transmittance of each filter. The absorption spectra of each cone cell and rod cell are overlaid in FIGS. 7A-7C, and the vertical axes in FIGS. 7A-7C show the normalized absorptance of each cell. The peak wavelength $P_S$ of sensitivity of the S cone cells is about 420 nm, the peak wavelength $P_M$ of sensitivity of the M cone cells is about 534 nm, the peak wavelength PI, of sensitivity of the L cone cells is about 564 nm, the peak wavelength $P_{Rod}$ of sensitivity of the rod cell is about 498 nm, and the wavelength of maximum sensitivity $P_{Pho}$ for the photopic vision is about 570 nm (see FIG. 3).

The filter 300B can change the transmittance of light at wavelengths equal to or longer than the peak wavelength $P_S$ (about 420 nm) of sensitivity of the S cone cells, and equal to or shorter than the peak wavelength $P_{Rod}$ (about 498 nm) of sensitivity of the, as indicated by the solid arrow in FIG. 7A. In other words, the lower limit of the bandwidth $B_B$ of the filter 300B is $P_S$ and the upper limit is the wavelength $P_{Rod}$. The lower limit of the bandwidth $B_B$ of filter 300B is not limited to $P_S$. The lower limit of bandwidth B may be set to a wavelength band shorter than P.

The filter 300B can change the transmittance of light in the blue wavelength band, and the upper limit of the bandwidth $B_B$ of the filter 300B is not limited to the peak wavelength $P_{Rod}$ (about 498 nm) of the rod cells. FIG. 7A shows another example of the upper limit of the bandwidth $B_B$ of filter 300B and the bandwidth $B_B$ at that time, indicated by the dotted arrows.

For example, the upper limit of the bandwidth $B_B$ of the filter 300B may be the wavelength $X_{Rod\text{-}M}$ (about 515 nm) at which the absorption spectrum of the rod cells intersects the absorption spectrum of the M cone cells. This wavelength $X_{Rod\text{-}M}$ is longer than the peak wavelength $P_{Rod}$ and shorter than the peak wavelength $P_M$ (about 534 nm) of M cone cells. Within the bandwidth longer than the wavelength $X_{Rod\text{-}M}$, the sensitivity of the rod cells is relatively small and the sensitivity of the M cone cells is relatively large. Therefore, if the upper limit of the bandwidth $B_B$ of the filter 300B is set longer than the wavelength $X_{Rod\text{-}M}$, the transmittance of light absorbed by the M cone cells (i.e., light in the green wavelength band) would be changed, and the visual characteristics of the subject 500 might not be appropriately corrected.

The upper limit of the bandwidth $B_B$ of filter 300B may be shorter than the peak wavelength $P_{Rod}$ (about 498 nm) of the sensitivity of rod cells. For example, the upper limit of the bandwidth $B_B$ of the filter 300B may be the wavelength $X_{S\text{-}Rod}$ (about 453 nm) at which the absorption spectrum of the S cone cells intersects that of the rod cells. This wavelength $X_{S\text{-}Rod}$ is longer than the peak wavelength $P_S$ and shorter than the peak wavelength $P_{Rod}$. Within the bandwidth shorter than the wavelength $X_{S\text{-}Rod}$, the sensitivity of the rod cells is relatively low and the sensitivity of the S cone cells is relatively high. Therefore, if the upper limit of the bandwidth $B_B$ of filter 300B is set shorter than the wavelength $X_{S\text{-}Rod}$, the percentage of light absorbed by the S cone cells will be larger, and the photosensitivity may not be appropriately corrected.

In order to appropriately correct for effects of the rod cells on photosensitivity, the bandwidth $B_B$ of filter 300B should include a wavelength band that is close to the peak wavelength $P_{Rod}$ of sensitivity of the rod cells. Therefore, the upper limit of the bandwidth $B_B$ of the filter 300B may be shorter than the peak wavelength $P_{Rod}$ of sensitivity of the rod cell, but should not be too far from the peak wavelength $P_{Rod}$. For example, if the difference between the peak wavelength $P_{Rod}$ of sensitivity of the rod cells, and the wavelength $X_{Rod\text{-}M}$ at which the absorption spectrum of the rod cells intersects that of the M cone cells is Δ, the upper limit of the bandwidth $B_B$ of filter 300B can be set within $P_{Rod} \pm \Delta$, it is possible to appropriately correct the effect of the rod cells on photosensitivity.

The filter 300G changes the transmittance of light at wavelengths equal to or longer than the peak wavelength $P_{Rod}$ (about 498 nm) of sensitivity of the rod cells and equal to or shorter than the wavelength $X_{M\text{-}L}$ (about 548 nm) where the absorption spectrum of the M cone cells intersects the absorption spectrum of the L cone cells, as shown in FIG. 7B with a solid line. This wavelength $X_{M\text{-}L}$ is longer than the peak wavelength $P_M$ and shorter than the peak wavelength $P_L$ (about 564 nm). In other words, the lower limit of the bandwidth $B_G$ of the filter 300G is the wavelength $P_{Rod}$ and the upper limit is the wavelength $X_{M\text{-}L}$.

In order to increase the percentage of light in the wavelength band to which the M-cone cell is sensitive among the light transmitted through the filter 300G, the lower limit of the bandwidth $B_G$ of the filter 300G may be set to the wavelength $X_{Rod\text{-}M}$ (about 515 nm) at which the absorption spectrum of the rod cells and that of M cone cells intersect. In this case, the bandwidth $B_G$ of the filter 300G is shown in FIG. 7B as a dotted line. With this configuration, only light in the wavelength band that is relatively more sensitive to the M cone cell compared to the rod cell and other cone cells will be absorbed or reflected by the filter 300G.

It is noted that the rod cells are cells that respond to light intensity and do not affect the color perception (color vision) of the subject. Therefore, even if the lower limit of the bandwidth $B_G$ of the filter 300G is set to the peak wavelength $P_{Rod}$ of sensitivity of the rod cells, the green light can be corrected.

The filter 300R is a filter that changes the transmittance of the red light for the subject 500 and has the characteristics of absorbing or reflecting light in the wavelength band to which the L cone cells are sensitive.

As shown by the solid line in FIG. 7C, the filter 300R allows light with wavelengths equal to or longer than the wavelength $X_{M\text{-}L}$ (about 548 nm), where the absorption spectrum of M cone cells intersects the absorption spectrum of the L cone cells to transmit. In other words, the lower limit of the bandwidth $B_R$ of filter 300R is the wavelength $X_{M\text{-}L}$.

In the wavelength band shorter than the wavelength $X_{M\text{-}L}$, the sensitivity of the L cone cells is lower and the sensitivity of the M cone cells is dominant. Therefore, if the lower limit of the bandwidth $B_R$ of the filter 300R is set shorter than the wavelength $X_{M\text{-}L}$, not only red light for the L cone cells but also green light may be absorbed or reflected.

The lower limit of the bandwidth $B_R$ of the filter 300R may be the wavelength $P_{Pho}$ (about 570 nm) at which the photopic vision is maximally sensitive, instead of the wavelength $X_{M\text{-}L}$.

Example 1 of Correction Filter

Next, an example of the correction filter will be explained. The transmittance of the bandwidth $B_B$ of the filter 300B is set based on the appropriate luminance $B_{CENTER}$ determined in S101. For example, if the appropriate luminance $B_{CENTER}$ is 70%, the transmittance of bandwidth $B_B$ is set to 70%. Thus, the light sensitivity of the subject 500 is corrected.

The transmittance of the bandwidth $B_G$ of filter 300G and the transmittance of the bandwidth $B_R$ of filter 300R are set based on the results of the tests in S102 and S103. For example, if the particular red component $R_{VALUE}$ is identified as −30% in the test of S102, the sensitivity of the subject 500 to red light is the same as the sensitivity of a healthy subject to red light. For example, if the particular green component $G_{VALUE}$ is identified as −50% in the test of S103, the sensitivity of the subject 500 to green light is lower than the sensitivity of the healthy human to red light. In this case, the transmittance of bandwidth $B_R$ of filter 300R is set lower than the transmittance of the bandwidth $B_G$ of the filter 300G by $|R_{VALUE}/G_{VALUE}|$ times. Thus, the difference between the sensitivity of the subject 500 to red light and the sensitivity to green light is corrected.

Figure 8:
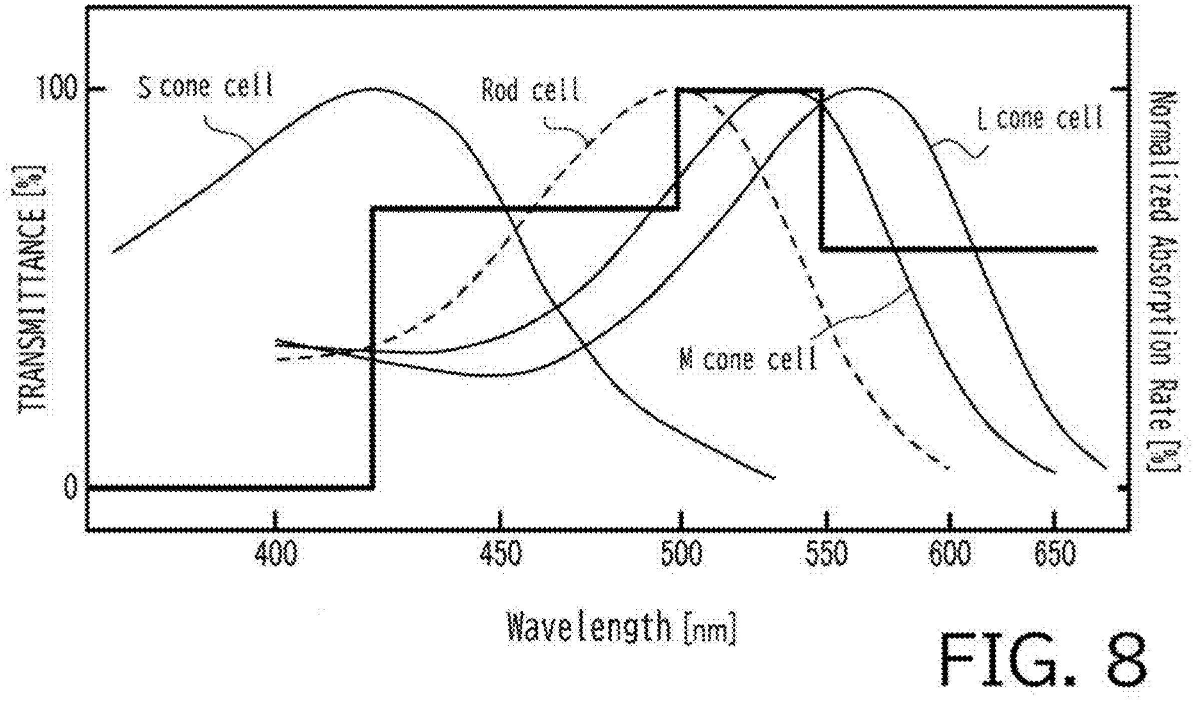
FIG. 8 shows an example of characteristics of the correction filter according to aspects of the present disclosure.

FIG. 8 shows an example of the characteristics of the correction filter 300 in the above example. The horizontal axis of FIG. 8 shows the wavelength [nm] and the vertical axis shows the transmittance [%] of the correction filter 300. In this example, the transmittance of the bandwidth $B_B$ of the filter 300B is set to 70%, the transmittance of bandwidth $B_G$ of the filter 300G is set to 100%, and the transmittance of the bandwidth $B_R$ of the filter 300R is lower than that of bandwidth $B_G$ of the filter 300G by $|R_{VALUE}/G_{VALUE}|$ times (i.e. 30/50=60%). The correction filter 300 has the combined characteristics of the three filters 300R, 300G, and 300B. By using this correction filter 300, it is possible to suppress the subject 500 feeling dazzled and to correct for the difference between the sensitivity of the subject 500 to red light and the sensitivity of the subject 500 to green light.

In the example shown in FIG. 8, the transmittance in the region with wavelengths shorter than the bandwidth $B_B$ is almost 0%. This is to reduce dazzling felt by the subject 500 who has photosensitivity. However, the photosensitivity of the subject 500 is corrected by reducing the transmittance in the bandwidth $B_B$ of the correction filter 300. The transmittance in the region with a wavelength shorter than bandwidth $B_B$ need not be 0%, for example, it may be the same as the transmittance in bandwidth $B_B$. In the example shown in FIG. 8, in bandwidth $B_R$, all wavelengths above $X_{M-L}$ (approximately 548 nm) are set to 60%. However, light with wavelengths longer than around 650 nm has low absorption in both cone and rod cells and has little effect on human color vision. Therefore, the transmittance of the correction filter 300 for light with wavelengths longer than around 650 nm may be set to any value.

Example 2 of Correction Filter

The transmittance of bandwidth $B_G$ of the filter 300G and the transmittance of bandwidth $B_R$ of the filter 300R may be based on the transmittance of bandwidth $B_B$ of filter 300B. For example, if the appropriate luminance $B_{CENTER}$ is 70%, the transmittance of bandwidth $B_B$ is set to 70%. If the particular red component $R_{VALUE}$ is identified as −30% and the particular green component $G_{VALUE}$ is identified as −50%, the transmittance of bandwidth $B_R$ of the filter 300R is set to $|R_{VALUE}/G_{VALUE}|$ times (70%×60%=42%) the 70% transmittance of bandwidth $B_B$. The transmittance of bandwidth $B_G$ of the filter 300G is set to 70%, the same as the transmittance of bandwidth $B_B$.

Figure 9:
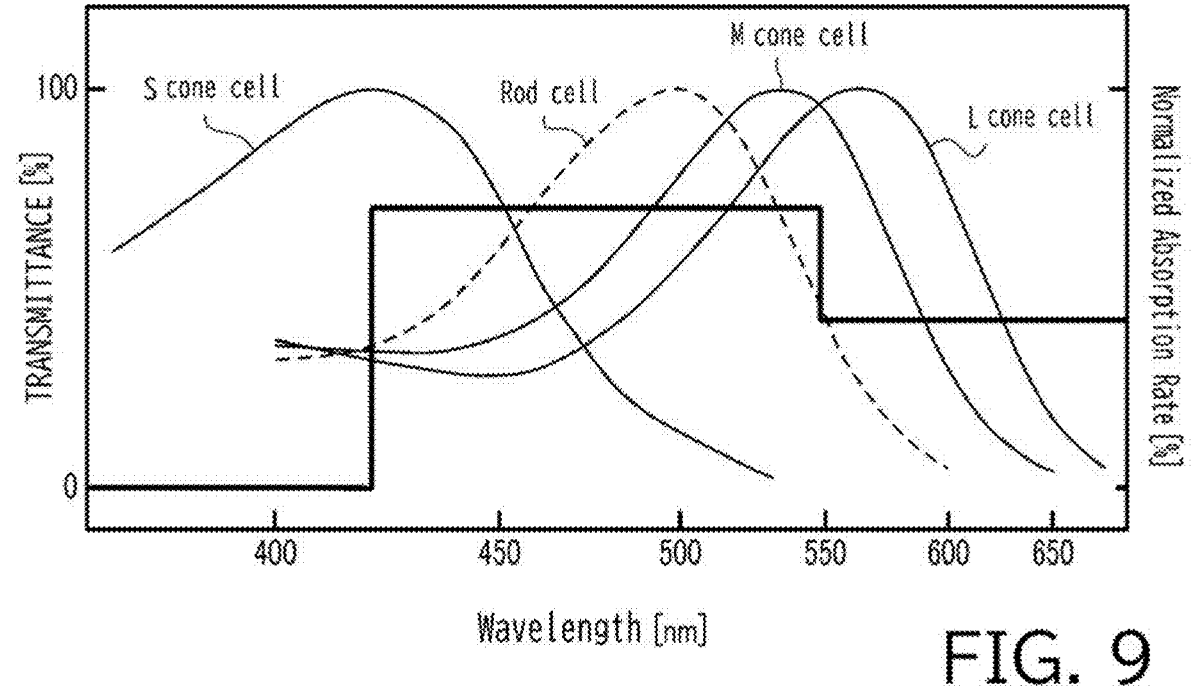
FIG. 9 shows an example of characteristics of the correction filter according to aspects of the present disclosure.

FIG. 9 shows an example of the characteristics of the correction filter 300 in the above example. The horizontal axis of FIG. 9 shows the wavelength [nm] and the vertical axis shows the transmittance [%] of the correction filter 300. In this example, the transmittance of bandwidth $B_B$ of the filter 300B and the transmittance of bandwidth $B_G$ of the filter 300G are set to 70%, and the transmittance of the bandwidth $B_R$ of the filter 300R is set to 42% (70%×60%). By using this correction filter 300, it is possible to reduce dazzling felt by the subject 500 and to correct for the difference between the sensitivity of the subject 500 to red light and the sensitivity of the subject 500 to green light.

Example 3 of Correction Filter

Next, an example of the correction filter 300 when the subject 500 does not have photosensitivity will be explained. If the subject 500 does not have photosensitivity and has low sensitivity to blue light, the transmittance of the bandwidth $B_B$ of the filter 300B, the transmittance of the bandwidth $B_G$ of the filter 300G, and the transmittance of the bandwidth $B_R$ of the filter 300R are set based on the test results of S101 to S103. For example, if the subject 500 can recognize the figure 121 in the background area 130 of the test image 110B in which a difference [%] of the blue component of the figure 121 from the background area 130 is −40% in test of S101, the sensitivity of the subject 500 to blue light is 75% (=30/40) of the sensitivity of a healthy human to blue light. For example, if the subject 500 can recognize the figure 121 in the background area 130 of the test image 110R in which a difference [%] of the red component of the figure 121 from the background area 130 is −30%, the sensitivity of the subject 500 to red light is the same as the sensitivity of the normal human to red light. For example, if the subject 500 can recognize the figure 121 in the background area 130 of the test image 110G in which a difference [%] of the green component of the figure 121 from the background area 130 is −50% in the test of S103, the sensitivity of the subject 500 to green light is 60% (=30/50) of the sensitivity of a healthy human to green light. Thus, by testing the degree to which the sensitivity of the subject 500 differs from the sensitivity of the healthy human for each color of RGB light, the ratio of the sensitivity of the subject 500 to RGB light can be determined. In the above example, the transmittance of the bandwidth $B_B$ of the filter 300B is set to 75% of the transmittance of bandwidth $B_G$ of the filter 300G. The transmittance of the bandwidth $B_R$ of the filter 300R is set to 60% of the transmittance of bandwidth Bo of the filter 300G.

Figure 10:
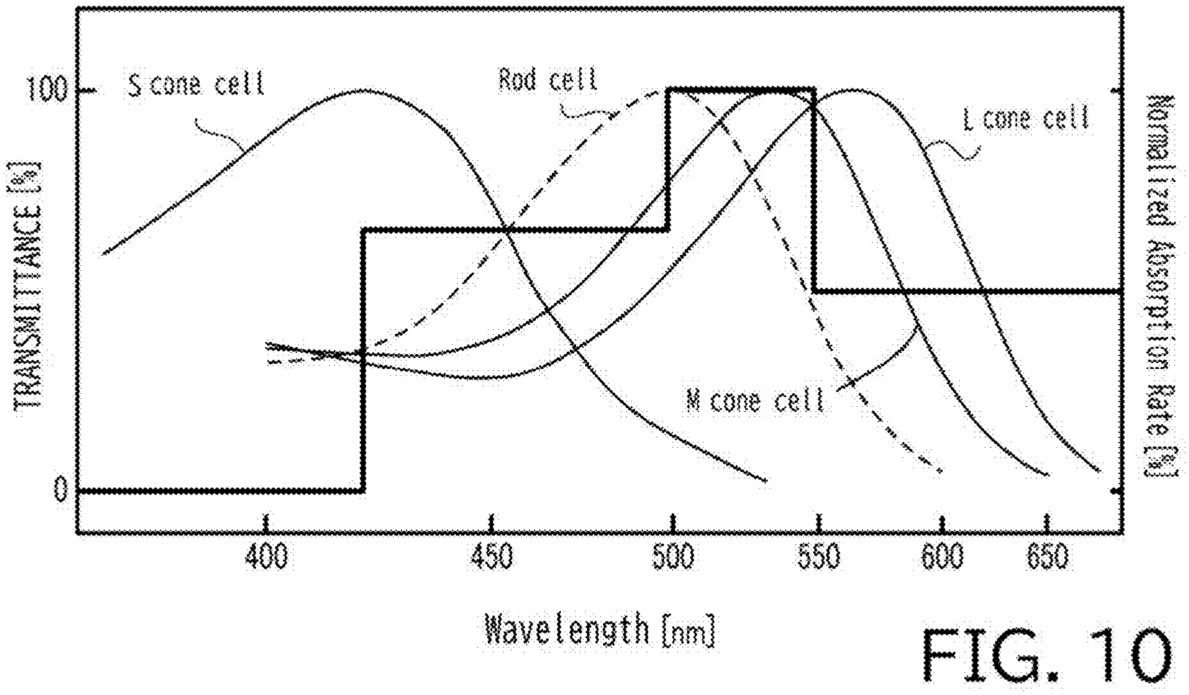
FIG. 10 shows an example of characteristics of the correction filter according to aspects of the present disclosure.

FIG. 10 shows an example of the characteristics of the correction filter 300 in the above example. The horizontal axis of FIG. 10 shows the wavelength [nm] and the vertical axis shows the transmittance [%] of the correction filter 300. In this example, the transmittance of bandwidth $B_G$ of the filter 300G is set to 100% because the subject 500 has the lowest sensitivity to green light among the three colors of RGB light. The transmittance of the bandwidth $B_B$ of the filter 300B is set to 75% of the transmittance of bandwidth $B_G$ of the filter 300G, and the transmittance of the bandwidth $B_R$ of the filter 300R is set to 60% of the transmittance of the bandwidth $B_G$ of the filter 300G. The correction filter 300 has a relatively high transmittance for green light, to which the subject 500 has low sensitivity, and a relatively low transmittance for red light, to which the subject 500 has high sensitivity (i.e., the same level as normal subjects). This allows to correct the difference in sensitivity of the RGB light of the subject 500.

The method of determining the characteristics of correction filter 300 using the results of the test of visual characteristics shown in FIG. 5 is not limited to the above example. For example, instead of using all of the test results from S101 to S103, only one or two of them may be used to determine the characteristics of the correction filter 300. Alternatively, instead of using the difference or ratio of the sensitivities to RGB light of the subject 500, each of the test results of S101-S103 may be used individually to determine the characteristics of the filters 300B, 300G, and 300R.

The characteristics of the correction filter 300 may be designed to match the visual characteristics of the subject 500. Alternatively, color filters with various characteristics may be prepared in advance, and the correction filter 300 may be made by combining multiple color filters according to the visual characteristics of the subject 500.

The results of the test of visual characteristics shown in FIG. 5 may be used for applications other than determining the characteristics of the correction filter 300. For example, the results of the test of visual characteristics shown in FIG. 5 may be used to adjust the luminance or color tone of a display (e.g., a personal computer, a portable terminal device, a television, etc.) or lighting device used by the subject 500.

Effect

According to this embodiment, the test image 110 has the background area 130 and the test area 120 located in the background area 130, and in the test area 120, and the test area 120 includes a figure 121 having a color different form a color of the background area 130 in a predetermined color component. By using this test image 110, the visual characteristics of the subject 500 for light of the particular color component can be efficiently tested.

According to this embodiment, by changing the luminance [%] of the background area 130 of the test image 110 in a one-dimensional manner, it is possible to test whether the subject 500 has photosensitive or not, or the degree of photosensitivity. In addition, by changing the blue component of the figure 121 in the test image 110B, the green component of the figure 121 in the test image 110G, and the red component of the figure 121 in the test image 110R, respectively, in one dimension, it is possible to test the sensitivity of the subject 500 to blue light, to green light, and to red light The sensitivity to blue light, sensitivity to green light, and sensitivity to red light of the subject 500. In this way, since the visual characteristics of the subject 500 can be measured by changing the luminance and particular color components in one dimension, rather than changing multiple color components of the test image 110, the load on the test can be reduced.

According to this embodiment, in the test image 110, the figure 121 has a color different from a color of the background area 130 in at least one of R, G or B components in the RGB color space, and the colors of the background area 130 and the figure 121 are the same in magnitude for any two of the RGB components. Therefore, when testing the visual characteristics of the subject 500 for the light of one of the remaining components, the difference in sensitivity of the subject 500 to the light of the other two components can be prevented from affecting the test. In the present disclosure, it is noted that the expression "at least one of A, B, or C" may have substantially the same meaning as "at least one of A, B, and/or C" and "at least one selected from a group consisting of A, B, and C."

According to this embodiment, the test image set includes a plurality of test images 110 in which the colors of the background area 130 are the same and the colors of the figures 121 are different from each other. Therefore, when the visual characteristics using the color of the figure 121 is tested, the color of the background area 130 can be suppressed from affecting the test results of the visual characteristics.

According to this embodiment, the test image set includes a plurality of test images 110 in which the color or the luminance of the background area 130 are different from each other. Therefore, by changing the color or luminance of the background area 130 of the test images 110, the degree of photosensitivity of the subject 500 can be tested.

In this embodiment, the test image 110B is used for testing the sensitivity of the subject 500 to blue light, the test image 110G is used for testing the sensitivity of the subject 500 to green light, and the test image 110R is used for testing the sensitivity of the subject 500 to red light. Thus, only the particular color to be tested among the three RGB colors can be tested.

The above is a description of an exemplary embodiment of the present disclosure. The embodiments of the present disclosure are not limited to those described above, and various modifications are possible within a scope of the technical concept of the invention. For example, the embodiments exemplary indicated in the specification or combinations of obvious embodiments as appropriate are also included in the embodiments of the present disclosure.

[Modification 1]

In the embodiment described above, the background area 130 of the test image 110 is achromatic and the figure 121 of the test area 120 is chromatic, but the embodiments of the present disclosure are not limited to this configuration. According to another embodiment of the present disclosure, both the background area 130 and the figure 121 may be colorful. For example, when testing whether or not the subject 500 has photosensitivity or the degree of photosensitivity of the subject 500, the blue component of the figure 121 in the test image 110B may be changed as well as the blue component of the background area 130.

Tables 4 through 14 show the input values (xR, xG, xB) of the background area 130 and the figure 121 of the test image 110B in another embodiment of the present disclosure. The background area 130 of the test image 110B may be achromatic or chromatic. The red and green components of the background area 130 are the same magnitude, and the blue component is equal to or smaller than the red and green components. The red and green components of figure 121 are the same magnitude as the red and green components of the background area 130, respectively. The blue component of figure 121 is smaller than the blue component of the background area 130.

TABLE 4

| | Luminance of Green and Red Component of Background Area [%] | | | | | |
|---|---|---|---|---|---|---|
| | 100% | 100% | 100% | 100% | 100% | 100% |
| | Luminance of Blue Component of Background Area [%] | | | | | |
| Difference of Blue Component of Figure | 100% | 90% | 80% | 70% | 60% | 50% |
| | Input Value of Background Area | | | | | |
| from Background Area [%] | (255, 255.255) | (255, 255, 243) | (255, 255, 230) | (255, 255, 217) | (255, 255, 202) | (255, 255, 186) |
| | Input Value of Figure | | | | | |
| −50% | (255, 255, 186) | (255, 255, 177) | (255, 255, 168) | (255, 255, 158) | (255, 255, 148) | (255, 255, 136) |
| −40% | (255, 255, 202) | (255, 255, 193) | (255, 255, 183) | (255, 255, 172) | (255, 255, 160) | 255, 255, 148) |
| −30% | (255, 255, 217) | (255, 255, 207) | (255, 255, 196) | (255, 255, 184) | (255, 255, 172) | (255, 255, 158) |
| −20% | (255, 255, 230) | (255, 255, 220) | (255, 255, 208) | (255, 255, 196) | (255, 255, 183) | (255, 255, 168) |
| −10% | (255, 255, 243) | (255, 255, 232) | (255, 255, 220) | (255, 255, 207) | (255, 255, 193) | (255, 255, 177) |

TABLE 4-continued

| Difference of Blue Component of Figure from Background Area [%] | Luminance of Green and Red Component of Background Area [%] | | | | |
|---|---|---|---|---|---|
| | 100% | 100% | 100% | 100% | 100% |
| | Luminance of Blue Component of Background Area [%] | | | | |
| | 40% | 30% | 20% | 10% | 5% |
| | Input Value of Background Area | | | | |
| | (255, 255, 168) | (255, 255, 148) | (255, 255, 123) | (255, 255, 90) | (255, 255, 65) |
| | Input Value of Figure | | | | |
| −50% | (255, 255, 123) | (255, 255, 108) | (255, 255, 90) | (255, 255, 65) | (255, 255, 48) |
| −40% | (255, 255, 133) | (255, 255, 117) | (255, 255, 97) | (255, 255, 71) | (255, 255, 52) |
| −30% | (255, 255, 143) | (255, 255, 125) | (255, 255, 104) | (255, 255, 76) | (255, 255, 56) |
| −20% | (255, 255, 152) | (255, 255, 133) | (255, 255, 111) | (255, 255, 81) | (255, 255, 59) |
| −10% | (255, 255, 160) | (255, 255, 141) | (255, 255, 117) | (255, 255, 85) | (255, 255, 62) |

TABLE 5

| Difference of Blue Component of Figure from Background Area [%] | Luminance of Green and Red Component of Background Area [%] | | | | |
|---|---|---|---|---|---|
| | 90% | 90% | 90% | 90% | 90% |
| | Luminance of Blue Component of Background Area [%] | | | | |
| | 90% | 80% | 70% | 60% | 50% |
| | Input Value of Background Area | | | | |
| | (243, 243, 243) | (243, 243, 230) | (243, 243, 217) | (243, 243, 202) | (243, 243, 186) |
| | Input Value of Figure | | | | |
| −50% | (243, 243, 177) | (243, 243, 168) | (243, 243, 158) | (243, 243, 148) | (243, 243, 136) |
| −40% | (243, 243, 193) | (243, 243, 183) | (243, 243, 172) | (243, 243, 160) | (243, 243, 148) |
| −30% | (243, 243, 207) | (243, 243, 196) | (243, 243, 184) | (243, 243, 172) | (243, 243, 158) |
| −20% | (243, 243, 220) | (243, 243, 208) | (243, 243, 196) | (243, 243, 183) | (243, 243, 168) |
| −10% | (243, 243, 232) | (243, 243, 220) | (243, 243, 207) | (243, 243, 193) | (243, 243, 177) |
| Difference of Blue Component of Figure from Background Area [%] | Luminance of Green and Red Component of Background Area [%] | | | | |
| | 90% | 90% | 90% | 90% | 90% |
| | Luminance of Blue Component of Background Area [%] | | | | |
| | 40% | 30% | 20% | 10% | 5% |
| | Input Value of Background Area | | | | |
| | (243, 243, 168) | (243, 243, 148) | (243, 243, 123) | (243, 243, 90) | (243, 243, 65) |
| | Input Value of Figure | | | | |
| −50% | (243, 243, 123) | (243, 243, 108) | (243, 243, 90) | (243, 243, 65) | (243, 243, 48) |
| −40% | (243, 243, 133) | (243, 243, 117) | (243, 243, 97) | (243, 243, 71) | (243, 243, 52) |
| −30% | (243, 243, 143) | (243, 243, 125) | (243, 243, 104) | (243, 243, 76) | (243, 243, 56) |
| −20% | (243, 243, 152) | (243, 243, 133) | (243, 243, 111) | (243, 243, 81) | (243, 243, 59) |
| −10% | (243, 243, 160) | (243, 243, 141) | (243, 243, 117) | (243, 243, 85) | (243, 243, 62) |

TABLE 6

| Difference of Blue Component of Figure from Background Area [%] | Luminance of Green and Red Component of Background Area [%] | | | | |
|---|---|---|---|---|---|
| | 80% | 80% | 80% | 80% | 80% |
| | Luminance of Blue Component of Background Area [%] | | | | |
| | 80% | 70% | 60% | 50% | 40% |
| | Input Value of Background Area | | | | |
| | (230, 230, 230) | (230, 230, 217) | (230, 230, 202) | (230, 230, 186) | (230, 230, 168) |
| | Input Value of Figure | | | | |
| −50% | (230, 230, 168) | (230, 230, 158) | (230, 230, 148) | (230, 230, 136) | (230, 230, 123) |
| −40% | (230, 230, 183) | (230, 230, 172) | (230, 230, 160) | (230, 230, 148) | (230, 230, 133) |

TABLE 6-continued

| | | | | | |
|---|---|---|---|---|---|
| −30% | (230, 230, 196) | (230, 230, 184) | (230, 230, 172) | (230, 230, 158) | (230, 230, 143) |
| −20% | (230, 230, 208) | (230, 230, 196) | (230, 230, 183) | (230, 230, 168) | (230, 230, 152) |
| −10% | (230, 230, 220) | (230, 230, 207) | (230, 230, 193) | (230, 230, 177) | (230, 230, 160) |

| | Luminance of Green and Red Component of Background Area [%] | | | |
|---|---|---|---|---|
| | 80% | 80% | 80% | 80% |
| | Luminance of Blue Component of Background Area [%] | | | |
| Difference of Blue Component of Figure | 30% | 20% | 10% | 5% |
| | Input Value of Background Area | | | |
| from Background Area [%] | (230, 230, 148) | (230, 230, 123) | (230, 230, 90) | (230, 230, 65) |
| | Input Value of Figure | | | |
| −50% | (230, 230, 108) | (230, 230, 90) | (230, 230, 65) | (230, 230, 48) |
| −40% | (230, 230, 117) | (230, 230, 97) | (230, 230, 71) | (230, 230, 52) |
| −30% | (230, 230, 125) | (230, 230, 104) | (230, 230, 76) | (230, 230, 56) |
| −20% | (230, 230, 133) | (230, 230, 111) | (230, 230, 81) | (230, 230, 59) |
| −10% | (230, 230, 141) | (230, 230, 117) | (230, 230, 85) | (230, 230, 62) |

TABLE 7

| | Luminance of Green and Red Component of Background Area [%] | | | |
|---|---|---|---|---|
| | 70% | 70% | 70% | 70% |
| | Luminance of Blue Component of Background Area [%] | | | |
| Difference of Blue Component of Figure | 70% | 60% | 50% | 40% |
| | Input Value of Background Area | | | |
| from Background Area [%] | (217, 217, 217) | (217, 217, 202) | (217, 217, 186) | (217, 217, 168) |
| | Input Value of Figure | | | |
| −50% | (217, 217, 158) | (217, 217, 148) | (217, 217, 136) | (217, 217, 123) |
| −40% | (217, 217, 172) | (217, 217, 160) | (217, 217, 148) | (217, 217, 133) |
| −30% | (217, 217, 184) | (217, 217, 172) | (217, 217, 158) | (217, 217, 143) |
| −20% | (217, 217, 196) | (217, 217, 183) | (217, 217, 168) | (217, 217, 152) |
| −10% | (217, 217, 207) | (217, 217, 193) | (217, 217, 177) | (217, 217, 160) |

| | Luminance of Green and Red Component of Background Area [%] | | | |
|---|---|---|---|---|
| | 70% | 70% | 70% | 70% |
| | Luminance of Blue Component of Background Area [%] | | | |
| Difference of Blue Component of Figure | 30% | 20% | 10% | 5% |
| | Input Value of Background Area | | | |
| from Background Area [%] | (217, 217, 148) | (217, 217, 123) | (217, 217, 90) | (217, 217, 65) |
| | Input Value of Figure | | | |
| −50% | (217, 217, 108) | (217, 217, 90) | (217, 217, 65) | (217, 217, 48) |
| −40% | (217, 217, 117) | (217, 217, 97) | (217, 217, 71) | (217, 217, 52) |
| −30% | (217, 217, 125) | (217, 217, 104) | (217, 217, 76) | (217, 217, 56) |
| −20% | (217, 217, 133) | (217, 217, 111) | (217, 217, 81) | (217, 217, 59) |
| −10% | (217, 217, 141) | (217, 217, 117) | (217, 217, 85) | (217, 217, 62) |

TABLE 8

| | Luminance of Green and Red Component of Background Area [%] | | | | | | |
|---|---|---|---|---|---|---|---|
| | 60% | 60% | 60% | 60% | 60% | 60% | 60% |
| | Luminance of Blue Component of Background Area [%] | | | | | | |
| Difference of Blue Component of Figure | 60% | 50% | 40% | 30% | 20% | 10% | 5% |
| | Input Value of Background Area | | | | | | |
| from Background Area [%] | (202, 202, 202) | (202, 202, 186) | (202, 202, 168) | (202, 202, 148) | (202, 202, 123) | (202, 202, 90) | (202, 202, 65) |
| | Input Value of Figure | | | | | | |
| −50% | (202, 202, 148) | (202, 202, 136) | (202, 202, 123) | (202, 202, 108) | (202, 202, 90) | (202, 202, 65) | (202, 202, 48) |
| −40% | (202, 202, 160) | (202, 202, 148) | (202, 202, 133) | (202, 202, 117) | (202, 202, 97) | (202, 202, 71) | (202, 202, 52) |
| −30% | (202, 202, 172) | (202, 202, 158) | (202, 202, 143) | (202, 202, 125) | (202, 202, 104) | (202, 202, 76) | (202, 202, 56) |

TABLE 8-continued

| Difference of Blue Component of Figure from Background Area [%] | Luminance of Green and Red Component of Background Area [%] | | | | | | |
|---|---|---|---|---|---|---|---|
| | 60% | 60% | 60% | 60% | 60% | 60% | 60% |
| | Luminance of Blue Component of Background Area [%] | | | | | | |
| | 60% | 50% | 40% | 30% | 20% | 10% | 5% |
| | Input Value of Background Area | | | | | | |
| | (202, 202, 202) | (202, 202, 186) | (202, 202, 168) | (202, 202, 148) | (202, 202, 123) | (202, 202, 90) | (202, 202, 65) |
| | Input Value of Figure | | | | | | |
| −20% | (202, 202, 183) | (202, 202, 168) | (202, 202, 152) | (202, 202, 133) | (202, 202, 111) | (202, 202, 81) | (202, 202, 59) |
| −10% | (202, 202, 193) | (202, 202, 177) | (202, 202, 160) | (202, 202, 141) | (202, 202, 117) | (202, 202, 85) | (202, 202, 62) |

TABLE 9

| Difference of Blue Component of Figure from Background Area [%] | Luminance of Green and Red Component of Background Area [%] | | | | | |
|---|---|---|---|---|---|---|
| | 50% | 50% | 50% | 50% | 50% | 50% |
| | Luminance of Blue Component of Background Area [%] | | | | | |
| | 50% | 40% | 30% | 20% | 10% | 5% |
| | Input Value of Background Area | | | | | |
| | (186, 186, 186) | (186, 186, 168) | (186, 186, 148) | (186, 186, 123) | (186, 186, 90) | (186, 186, 65) |
| | Input Value of Figure | | | | | |
| −50% | (186, 186, 136) | (186, 186, 123) | (186, 186, 108) | (186, 186, 90) | (186, 186, 65) | (186, 186, 48) |
| −40% | (186, 186, 148) | (186, 186, 133) | (186, 186, 117) | (186, 186, 97) | (186, 186, 71) | (186, 186, 52) |
| −30% | (186, 186, 158) | (186, 186, 143) | (186, 186, 125) | (186, 186, 104) | (186, 186, 76) | (186, 186, 56) |
| −20% | (186, 186, 168) | (186, 186, 152) | (186, 186, 133) | (186, 186, 111) | (186, 186, 81) | (186, 186, 59) |
| −10% | (186, 186, 177) | (186, 186, 160) | (186, 186, 141) | (186, 186, 117) | (186, 186, 85) | (186, 186, 62) |

TABLE 10

| Luminance of Green and Red Component of Background Area [%] | 40% | 40% | 40% | 40% | 40% |
|---|---|---|---|---|---|
| Luminance of Blue Component of Background Area [%] | 40% | 30% | 20% | 10% | 5% |
| Input Value of Background Area | (168, 168, 168) | (168, 168, 148) | (168, 168, 123) | (168, 168, 90) | (168, 168, 65) |
| Difference of Blue Component of Figure from Background Area [%] | Input Value of Figure | | | | |
| −50% | (168, 168, 123) | (168, 168, 108) | (168, 168, 90) | (168, 168, 65) | (168, 168, 48) |
| −40% | (168, 168, 133) | (168, 168, 117) | (168, 168, 97) | (168, 168, 71) | (168, 168, 52) |
| −30% | (168, 168, 143) | (168, 168, 125) | (168, 168, 104) | (168, 168, 76) | (168, 168, 56) |
| −20% | (168, 168, 152) | (168, 168, 133) | (168, 168, 111) | (168, 168, 81) | (168, 168, 59) |
| −10% | (168, 168, 160) | (168, 168, 141) | (168, 168, 117) | (168, 168, 85) | (168, 168, 62) |

TABLE 11

| Luminance of Green and Red Component of Background Area [%] | 30% | 30% | 30% | 30% |
|---|---|---|---|---|
| Luminance of Blue Component of Background Area [%] | 30% | 20% | 10% | 5% |

TABLE 11-continued

| | | | | |
|---|---|---|---|---|
| Input Value of Background Area | (148, 148, 148) | (148, 148, 123) | (148, 148, 90) | (148, 148, 65) |
| Difference of Blue Component of Figure from Background Area [%] | Input Value of Figure | | | |
| −50% | (148, 148, 108) | (148, 148, 90) | (148, 148, 65) | (148, 148, 48) |
| −40% | (148, 148, 117) | (148, 148, 97) | (148, 148, 71) | (148, 148, 52) |
| −30% | (148, 148, 125) | (148, 148, 104) | (148, 148, 76) | (148, 148, 56) |
| −20% | (148, 148, 133) | (148, 148, 111) | (148, 148, 81) | (148, 148, 59) |
| −10% | (148, 148, 141) | (148, 148, 117) | (148, 148, 85) | (148, 148, 62) |

TABLE 12

| | | | |
|---|---|---|---|
| Luminance of Green and Red Component of Background Area [%] | 20% | 20% | 20% |
| Luminance of Blue Component of Background Area [%] | 20% | 10% | 5% |
| Input Value of Background Area | (123, 123, 123) | (123, 123, 90) | (123, 123, 65) |
| Difference of Blue Component of Figure from Background Area [%] | Input Value of Figure | | |
| −50% | (123, 123, 90) | (123, 123, 65) | (123, 123, 48) |
| −40% | (123, 123, 97) | (123, 123, 71) | (123, 123, 52) |
| −30% | (123, 123, 104) | (123, 123, 76) | (123, 123, 56) |
| −20% | (123, 123, 111) | (123, 123, 81) | (123, 123, 59) |
| −10% | (123, 123, 117) | (123, 123, 85) | (123, 123, 62) |

TABLE 13

| | | |
|---|---|---|
| Luminance of Green and Red Component of Background Area [%] | 10% | 10% |
| Luminance of Blue Component of Background Area [%] | 10% | 5% |
| Input Value of Background Area | (90, 90, 90) | (90, 90, 65) |
| Difference of Blue Component of Figure from Background Area [%] | Input Value of Figure | |
| −50% | (90, 90, 65) | (90, 90, 48) |
| −40% | (90, 90, 71) | (90, 90, 52) |
| −30% | (90, 90, 76) | (90, 90, 56) |
| −20% | (90, 90, 81) | (90, 90, 59) |
| −10% | (90, 90, 85) | (90, 90, 62) |

TABLE 14

| | |
|---|---|
| Luminance of Green and Red Component of Background Area [%] | 5% |
| Luminance of Blue Component of Background Area [%] | 5% |
| Input Value of Background Area | (65, 65, 65) |
| Difference of Blue Component of Figure from Background Area [%] | Input Value of Figure |

TABLE 14-continued

| | |
|---|---|
| −50% | (65, 65, 48) |
| −40% | (65, 65, 52) |
| −30% | (65, 65, 56) |
| −20% | (65, 65, 59) |
| −10% | (65,65, 62) |

The "Luminance of Red and Green Components of Background area [%]" in the tables 4 through 14 represent the luminances of the red and green components of the background area 130 in a case where the luminance is 100% when the input value of the red and green components of the background area 130 is 255. The "Luminance of Blue Component of Background Area [%]" represents the luminance of the blue component of the background area 130 in a case where the luminance is 100% when the input value of the blue component of the background area 130 is 255. The "Input Value of Background Area" indicates an input value (xR, xG, xB) at the respective luminance [%] of the background area 130. In this embodiment, the test images 110B shown in the table 4 through table 14 differ from each other in the magnitude of the red and green components of the background area 130. If the luminance of the input values of the red and green components is 100% when the input value of the red and green components is 255, the luminances of the red and green components of the background area 130 of the test images 110B, which are shown in the table 4 to table 14, are 100%, 90%, 80%, 70%, 60%, 50%, 40%, 30%, 20%, 10%, and 5%, respectively.

The "Difference [%] of Blue Component of Figure from Background Area" in the tables 4 through 14 represent the luminances of the blue component of the figure 121 as the difference from the luminance of the blue component of the background area 130, when the luminance of the blue component of the background area 130 is 100%. In this embodiment, there are five types of blue component [%] of the figure 121, from −50% to −10% in 10% increments.

The test image 110B is a combination of the background area 130 and the FIG. 121 with the input values listed in the same column as the background area 130. For example, there are five types of test images 110B in which the input value of the background area 130 is (255, 255, 255), and the red and green components of the figure 121 of these five types of test images 110B are the same magnitude as the red and green components of the background area 130, respectively (i.e., both 255). On the other hand, the blue input values of the figures 121 in these five test images 110B are set to change in luminance from −50% to −10% in 10% increments with respect to the blue input values of the background area 130, respectively. The input values of the blue components of the figure 121 of the five types of the test images 110B are 186, 202, 217, 230, and 243, respectively.

The test images 110B listed in the table 4 through table 14 have the luminance of the background area 130 and the figure 121 decreasing from the table 4 to the table 14. One test image 110B from each of the table 4 to the table 14 is selected and sequentially displayed on the display 100. Then, by testing whether or not the subject 500 feels dazzled to the test image 110B, it can be tested whether or not the subject 500 has photosensitivity or the degree of photosensitivity of the subject 500.

Among the test images 110B that the subject 500 did not feel dazzled, a table containing the test images 110B with the highest luminance of the background area 130 and the figure 121 is selected from the tables 4 to the table 14. Then, the test images 110B shown in the selected table are selected one by one and sequentially displayed on the display 100. The sensitivity of the subject 500 to blue light can be tested by selecting one of the sequentially displayed test images 110B in which the subject 500 can recognize the figure 121 in the background area 130.

Although the tables 4 to the table 14 show modifications of the test images 110B in which the blue component of the figure 121 is changed with respect to the color of the background area 130, the embodiments of the present disclosure are not limited to those. For example, the test image 110R in which the red component of the figure 121 is changed with respect to the color of the background area 130 or the test image 110G in which the green component of the figure 121 is changed with respect to the color of the background area 130 may be used to test the visual characteristics of the subject 500.

[Modification 2]

For example, in the embodiment described above, the test image 110 has only one shape 121 having a single color located in the test area 120, but the embodiment is not limited to this configuration. Two or more figures of different colors from each other may be arranged in the test area of the test image.

Figure 11:
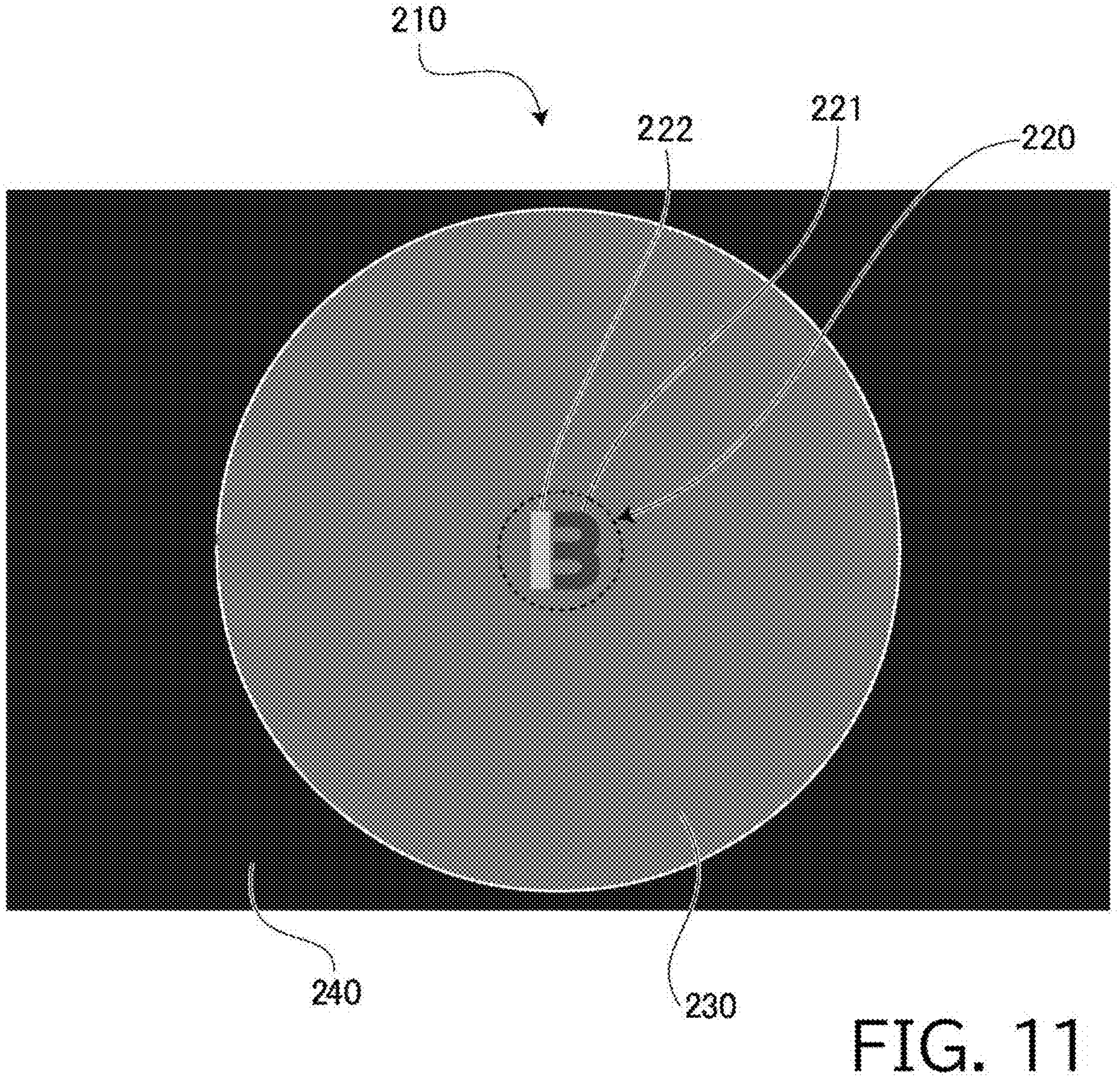
FIG. 11 shows an example of a test image according to aspects of the present disclosure.

FIG. 11 shows a test image 210 in another embodiment of the present disclosure. The test image 210 has a test area 220 around a center of the test image 210 and a background area 230 surrounding the test area 220. Similar to the test image 110, the test area 220 of the test image 210 is an area corresponding to the fovea centralis of a human retina, and the background area 230 corresponds to an area surrounding the fovea centralis of the human retina. It is preferable that a peripheral area 240 further outside of the background area 230 is black.

The test area 220 includes a FIG. 221 having a different color from a color of the background area 230 in a magnitude of a green component, and a FIG. 222 having a different color from a color of the background area 230 in a magnitude of a red component. The green component of the FIG. 221 and the red component of the FIG. 222 can be changed independently. By using this test image 210, both the sensitivity of the subject 500 to green light and the sensitivity of the subject 500 to red light can be tested.

A shape and a color of figures to be located in the test area 220 are not limited to those shown in FIG. 11. For example, the FIG. 222 may be located inside a FIG. 221. In addition, any two or all three of the following may be located in the test area 220: a figure having a color different from a color of the background area 230 in a magnitude of a blue component, a figure having a color different from a color of the background area 230 in a magnitude of green component, and a figure having a color different from a color of the background area 230 in a magnitude of green component.

OTHER MODIFICATIONS

In the above embodiment, the test image 110 is displayed on the display 100, but embodiments of the present disclosure are not limited to this configuration. The test image 110 may be printed on a sheet or a board. In this case, a plurality of the test images 110 with different luminances of the background areas 130 or luminance of the figures 121 are printed on different the sheet or the boards. The printed plurality of the test images 110 are sequentially placed at a predetermined distance from the subject 500 and illuminated with white illumination light to present them to the subject 500. With this configuration, the visual characteristics of the subject 500 can be tested. It is preferable that the printed test images 110 is placed where a background is black.

What is claimed is:

1. A test image set for testing visual characteristics of a subject, the test image set including a plurality of test images, wherein each of the plurality of test images includes:

a background area; and a test area located in the background area, the test area including a figure having a color different from a color of the background area in at least one of R, G or B components in a RGB color space, wherein the test area is located in such a manner that light emitted from the test area forms an image within a fovea centralis of the subject when the subject looks at around a center of the test image, wherein a color of an area, in the test area, where the figure is not located has the same color as the color of the background area, and wherein the plurality of test images are different from each other in the color of at least one of the background area or the figure.

2. The test image set for testing the visual characteristics according to claim 1, wherein a luminance of the color of the figure is different from a luminance of the color of the background area in at least one particular component among the R, G and B components.

3. The test image set for testing the visual characteristics according to claim 2, wherein magnitudes of two components other than the particular component among the R, G and B components of the color of the figure are the same as each other.

4. The test image set for testing the visual characteristics according to claim 1, including the plurality of test images in which colors of the background areas are the same as each other and colors of the figures are different from each other.

5. The test image set for testing the visual characteristics according to claim 1, including the plurality of test images in which colors of the background areas are different from each other.

6. The test image set for testing the visual characteristics according to claim 5, including the plurality of test images in which magnitudes of one of the R, G and B components of colors of the figures are different from each other.

7. The test image set for testing the visual characteristics according to claim 5, wherein magnitudes of two components among the R, G and B components of the color of the figure are the same as each other.

8. The test image set for testing the visual characteristics according to claim 1, wherein the background area has a chromatic color.

9. The test image set for testing the visual characteristics according to claim 1, wherein the test area is located in such a manner that light emitted from the test area forms an image within a viewing angle of the subject of 2 degrees with respect to a center of a retina of the subject when the subject looks at around a center of the test image.

10. A test method for visual characteristics of a subject using test images included in a test image set according to claim 1, the test method for visual characteristics comprising:

sequentially showing the test images included in the test image set to the subject;

determining whether a particular test condition is satisfied when the subject looks at each of the test images sequentially shown in the showing; and specifying, among the test images included in the test image set, a test image that satisfies the particular test condition.

11. The test method for visual characteristics according to claim 10, wherein the particular condition includes a first test condition where the subject can recognize the figure located in the test area of the test image when the subject looks at the test image.

12. The test method for visual characteristics according to claim 11, wherein the first test condition is a condition where the subject can recognize the figure located in the test area without feeling dazzled to the test image when the subject looks at the test image.

13. The test method for visual characteristics according to claim 11, wherein, when there are a plurality of test images that satisfy the first test condition, one of the plurality of test images that satisfy the first test condition is specified in the specifying.

14. The test method for visual characteristics according to claim 13, wherein, in the specifying, the test image including the background area with a central value of luminances of a plurality of background areas of the plurality of test images that satisfy the first test condition or the closest value of the central value is specified.

15. The test method for visual characteristics according to claim 13, wherein the test image including the background area with the highest luminance among the plurality of test images that satisfy the first test condition is specified in the specifying.

16. The test method for visual characteristics according to claim 15, wherein, when there are a plurality of test images that satisfy the second test condition, a test image, in which the color of the background area and the color of the figure are closest to each other among the plurality of test images that satisfy the second test condition, is specified in the specifying.

17. The test method for visual characteristics according to claim 13, wherein the particular test condition includes a second test condition where the subject can recognize difference between the color of the background area and the color of the figure when the subject looks at the test image.

18. The test method for visual characteristics according to claim 17, wherein the second test condition is a condition where the subject can recognize difference between the color of the background area and the color of the figure and the figure located in the test area of the test image when the subject looks at the test image.

19. A determining method for determining characteristics of correction filter using a test image set including a plurality of test images according to claim 1, the determining method comprising:

sequentially showing the test images included in the test image set to the subject;

determining whether a particular test condition is satisfied when the subject looks at each of the test images sequentially shown;

specifying, among the test images, at least one test image that satisfies the particular test condition; and determining transmittance of a correction filter configured to adjust an intensity of transmitted light based on a color of the specified at least one test image.

20. A correction filter having the transmittance determined by the determining method for characteristics of correction filter according to claim 19.

21. A determining method for determining characteristics of correction filter using a test image set including a plurality of test images according to claim 1, the determining method comprising:

sequentially showing the test images included in the test image set to the subject;

determining whether a particular test condition is satisfied when the subject looks at each of the test images sequentially shown; and specifying, among the test images, at least one test image that satisfies the particular test condition, wherein the particular condition includes a first test condition where the subject can recognize the figure located in the test area of the test image when the subject looks at the test image, and wherein the determining method further comprises determining transmittance of a particular wavelength band of a correction filter configured to adjust an intensity of transmitted light based on color(s) of the background area of the specified at least one test image.

22. A correction filter having the transmittance determined by the determining method for characteristics of correction filter according to claim 21.

23. A determining method for determining characteristics of correction filter using a test image set including a plurality of test images according to claim 1, the determining method comprising:

sequentially showing the test images included in the test image set to the subject;

determining whether a particular test condition is satisfied when the subject looks at each of the test images sequentially shown; and specifying, among the test images, at least one test image that satisfies the particular test condition, wherein the particular test condition includes a second test condition where the subject can recognize difference between the color of the background area and the color of the figure when the subject looks at the test image, and wherein the determining method further comprises determining transmittance of a particular wavelength band of a correction filter configured to adjust an intensity of transmitted light based on color(s) of the background area(s) of the test image(s) which specified in the test method, wherein, in the test image satisfying the second test condition, the determined transmittance is higher as a magnitude of a particular color component of the background area and a magnitude of the particular color component of the figure become closer.

24. A correction filter having the transmittance determined by the determining method for characteristics of correction filter according to claim 23.

25. The test image set for testing the visual characteristics according to claim 1, wherein the figure has a circular shape.

26. A test image set for testing visual characteristics of a subject, the test image set including a plurality of test images wherein each of the plurality of test images includes:

a background area; and a test area located in the background area, wherein the plurality of test images include:

a plurality of red color test images each of which has a figure located in a corresponding test area, each figure having a color different from a color of a corresponding background area in an R component in an RGB color space, the R components of the figures in the plurality of red color test images being different from each other; and a plurality of green color test images each of which has a figure located in a corresponding test area, each figure having a color different from a color of a corresponding background area in a G component in the RGB color space, the G components of the figures in the plurality of green color test images being different from each other.

27. A test method for visual characteristics of a subject using a plurality of test images included in a test image set according to claim 26, the test method for visual characteristics comprising:

sequentially showing the plurality of red color test images to the subject;

determining whether a particular test condition is satisfied when the subject looks at each of the plurality of red color test images sequentially shown; and specifying, among the plurality of red color test images, a red color test image that satisfies the particular test condition sequentially showing the plurality of green color test images to the subject;

determining whether the particular test condition is satisfied when the subject looks each of at the plurality of green color test images sequentially shown; and specifying, among the plurality of green color test images, a green color test image that satisfies the particular test condition, and determining a ratio of a sensitivity to red light to a sensitivity to green light of the subject based on the R component of the figure of the specified red color test image and the G component of the figure of the specified green color test image.

* * * * *